United States Patent
Nelson

(10) Patent No.: US 6,664,388 B2
(45) Date of Patent: Dec. 16, 2003

(54) REAGENTS FOR OLIGONUCLEOTIDE CLEAVAGE AND DEPROTECTION

(75) Inventor: Jeffrey S. Nelson, Woodinville, WA (US)

(73) Assignee: Applera Corporation, Foster City, CA (US)

(*) Notice: Subject to any disclaimer, the term of this patent is extended or adjusted under 35 U.S.C. 154(b) by 0 days.

(21) Appl. No.: 10/091,231

(22) Filed: Mar. 4, 2002

(65) Prior Publication Data

US 2003/0181712 A1 Sep. 25, 2003

Related U.S. Application Data

(60) Provisional application No. 60/274,309, filed on Mar. 8, 2001.

(51) Int. Cl.$^7$ ............................................. C07H 21/04
(52) U.S. Cl. ........................... 536/25.31; 536/25.32; 536/25.33; 536/25.34; 536/25.4; 536/27.3; 536/28.1; 536/29.1
(58) Field of Search ................ 536/25.31, 25.32, 536/25.33, 25.34, 25.4, 25.3, 27.1, 28.1, 29.1

(56) References Cited

U.S. PATENT DOCUMENTS

| | | |
|---|---|---|
| 4,965,349 A | 10/1990 | Woo et al. |
| 5,514,789 A | 5/1996 | Kempe |
| 5,656,741 A | 8/1997 | Chow et al. |
| 5,738,829 A | 4/1998 | Kempe |
| 5,801,155 A | 9/1998 | Kutyavin et al. |
| 5,932,718 A | 8/1999 | Letsinger et al. |
| 5,935,527 A | 8/1999 | Andrus et al. |
| 5,936,077 A | 8/1999 | Pfleiderer et al. |

FOREIGN PATENT DOCUMENTS

| | | |
|---|---|---|
| DE | 196 27 898 A1 | 1/1998 |
| EP | 0 839 829 A2 | 5/1998 |
| EP | 1 028 124 A2 | 8/2000 |
| WO | WO 96/03417 A1 | 2/1996 |
| WO | WO 96/32496 A2 | 10/1996 |
| WO | WO 00/46231 A1 | 8/2000 |

OTHER PUBLICATIONS

Search Report from PCT/US02/06739 mailed Oct. 29, 2002.

Aubert et al., "Optimized synthesis of phosphorothioate oligodeoxyribonucleotides substituted with a 5'–protected thiol function and a 3'–amino group," *Nucleic Acids Research*, vol. 28, No. 3, pp. 818–825 (2000).

Baier et al., "Synthesis and Purification in a Single colum on a High–Throughput Automated Oligonucleotide Production System," *BioTechniques*, vol. 20, No. 2, pp. 298–303 (Feb. 1996).

Boal et al., "Cleavage of oligodeoxyribonucleotides from controlled–pore glass supports and their rapid deprotection by gaseous amines," *Nucleic Acids Research*, vol. 24, No. 15, pp. 3115–3117 (1996).

Chang et al., "An Improved Deprotection Procedure of Amine–Containing Oligonucleotides from Acrylonitrile Modification," *Nucleosides & Nucleotides*, 18(6&7), pp. 1205–1206 (1999).

Kutyavin et al., "3'–Minor groove binder–DNA probes increase sequence specificity at PCR extension temperatures," *Nucleic Acids Research*, vol. 28, No. 2, pp. 655–661 (2000).

Manoharan et al., "A New Protecting Group Strategy for Amino Groups in Oligonucleotide Chemistry: CEOC Group," *Nucleosides & Nucleotides*, 18(6&7), pp. 1199–1201 (1999).

Polushin et al, "On the rapid deprotection of synthetic oligonucleotides and analogs," *Nucleic Acids Research*, vol. 22, No. 4, pp. 639–645 (1994).

(List continued on next page.)

*Primary Examiner*—James O. Wilson
*Assistant Examiner*—Traviss C. McIntosh, III
(74) *Attorney, Agent, or Firm*—Alex Andrus; Vincent M. Powers

(57) ABSTRACT

The present invention provides a process for the removal of protecting groups, i.e. deprotection, from chemically synthesized oligonucleotides. In one embodiment, the invention provides reagents suitable for use in such a process, and kits incorporating such reagents in a convenient, ready-to-use format. By use of the process and reagents of the invention, side-reactions leading to certain impurities that contaminate the synthesized oligonucleotides can be minimized.

Methods and reagents are provided for deprotection of an oligonucleotide by reacting a protected oligonucleotide with a deprotection reagent wherein the deprotection reagent comprises an active methylene compound and an amine reagent. The active methylene compound has the structure:

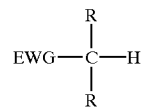

where substituent EWG is an electron-withdrawing group and R is hydrogen, $C_1$–$C_{12}$ alkyl, $C_6$–$C_{20}$ aryl, heterocycle or an electron-withdrawing group.

61 Claims, 7 Drawing Sheets

OTHER PUBLICATIONS

Pon et al., "Hydroquinone–O,O'–diacetic acid (Q–linker) as a replacement for succinyl and oxalyl linker arms in solid phase oligonucleotide synthesis," *Nucleic Acids Research*, vol. 25, No. 18, pp. 3629–3635, (1997).

Reddy et al., "Ultrafast Cleavage and Deprotection of Oligonucleotides Synthesis and Use of $C^{Ac}$ Derivatives," *Nucleosides & Nucleotides*, 16(7–9), pp. 1589–1598 (1997).

Surzhikov et al., "Advanced method for oligonucleotide deprotection," *Nucleic Acids Research*, vol. 28, No. 8, ℮ 29 (2000).

Theisen et al., "N–6–Dialkylformamidiine–2'–Deoxyadenosine Phosphoramidites in Oligodeoxynucleotide Synthesis. Rapid Deprotection of Oligodeoxynucleotides.," *Nucleosides & Nucleotides*, 12(10), pp. 1033–1046 (1993).

Wilk et al., "The 4–[N–Methyl–N–(2,2,2–trifluoroacetyl)amino] butyl Group as an Alternative to the 2–Cyanoethyl Group for Phosphate Protection in the Synthesis of Oligodeoxyribonucleotides," *J. Org. Chem.*, vol. 64, No. 20, pp. 7515–7522 (1999).

SEQUENCE LISTING

```
<160> NUMBER OF SEQ ID NOS: 6

<210> SEQ ID NO 1
<211> LENGTH: 8
<212> TYPE: DNA
<213> ORGANISM: Unknown
<220> FEATURE:
<223> OTHER INFORMATION: Synthetic DNA

<400> SEQUENCE: 1 tttttttt                                                            8

<210> SEQ ID NO 2
<211> LENGTH: 15
<212> TYPE: DNA
<213> ORGANISM: Unknown
<220> FEATURE:
<223> OTHER INFORMATION: Synthetic DNA

<400> SEQUENCE: 2
tttttttttt ttttt                                                   15

<210> SEQ ID NO 3
<211> LENGTH: 13
<212> TYPE: DNA
<213> ORGANISM: Unknown
<220> FEATURE:
<223> OTHER INFORMATION: Synthetic DNA

<400> SEQUENCE: 3
cagtcgccct gcc                                                     13

<210> SEQ ID NO 4
<211> LENGTH: 15
<212> TYPE: DNA
<213> ORGANISM: Unknown
<220> FEATURE:
<223> OTHER INFORMATION: Synthetic DNA

<400> SEQUENCE: 4
cttcttgcta attcc                                                   15

<210> SEQ ID NO 5
<211> LENGTH: 13
<212> TYPE: DNA
```

```
-continued

<213> ORGANISM: Unknown
<220> FEATURE:
<223> OTHER INFORMATION: Synthetic DNA

<400> SEQUENCE: 5
ccatgcgtta gcc                                                          13

<210> SEQ ID NO 6
<211> LENGTH: 25
<212> TYPE: DNA
<213> ORGANISM: Unknown
<220> FEATURE:
<223> OTHER INFORMATION: Synthetic DNA

<400> SEQUENCE: 6
aaaatcaaga actacaagac cgccc                                             25
```

REAGENTS FOR OLIGONUCLEOTIDE CLEAVAGE AND DEPROTECTION

I. CROSS REFERENCE TO RELATED APPLICATIONS

This non-provisional application claims the benefit under 35 USC §119(e) of provisional application Ser. No. 60/274,309, filed Mar. 8, 2001, which is incorporated herein by reference.

II. FIELD OF THE INVENTION

This invention relates generally to synthetic oligonucleotide compounds. More specifically, this invention relates to cleavage of oligonucleotides from solid supports and deprotection of oligonucleotides.

III. BACKGROUND OF THE INVENTION

Oligonucleotides are essential reagents in many important molecular biology experiments, assays and information gathering operations, such as the polymerase chain reaction (PCR), diagnostic probes, single nucleotide polymorphism (SNP) detection, and genomic sequencing. The benefits of conducting the synthesis of oligonucleotides by the sequential addition and covalent attachment of monomeric units onto a solid support is well appreciated. In particular, the method of Caruthers is highly optimized and almost universally adopted (U.S. Pat. Nos. 4,458,066 and 4,973,679). The vast majority of the millions of oligonucleotides consumed each year are prepared by automated synthesis with phosphoramidite nucleoside monomers (Beaucage (1992) Tetrahedron Lett. 22:1859–62; U.S. Pat. No. 4,415,732).

Conducting chemical reactions on solid supports has several practical advantages: (i) excess reagents and soluble by-products can be easily removed and separated by simple washing and filtration steps, (ii) dispensing, manipulating, organizing the parallel production of many oligonucleotides is facilitated, and (iii) reactions can be scaled up or down for economy and ease of handling.

Many applications utilize oligonucleotides with a covalently attached label. Labels may impart some function, e.g. affinity, detection, or other physical property. Oligonucleotide labels often have reactive functionality, which may preferably be protected to minimize side reactions and modifications.

Upon completion of synthesis, the solid support-bound oligonucleotide is removed from the support by chemical cleavage of the covalent linkage between the oligonucleotide and the solid support, and deprotected to remove all remaining protecting groups from the oligonucleotide. The steps of cleavage and deprotection may be concurrent and conducted with the same reagent. Alternatively, cleavage and deprotection may be conducted at different temperatures and with different reagents.

Typically, cleavage of the oligonucleotide (20 nmole to 1 $\mu$mole) from the solid support is performed in the synthesis column at room temperature using about 1 to 3 ml concentrated ammonium hydroxide $NH_4OH$ (about 28–30% $NH_3$ in water). Cleavage of the typical ester linkage at the 3' terminus of the oligonucleotide is complete in about one hour under these conditions. While the linkage between the oligonucleotide and the solid support is cleaving, ammonium hydroxide is also removing the 2-cyanoethyl groups from the internucleotide phosphates and the nucleobase protecting groups. Depending on the nucleobase and the type of protecting groups, deprotection (removal of protecting groups) of the oligonucleotide requires approximately 1 to 8 hours at 55° C. treatment with concentrated ammonium hydroxide.

Alternatively, cleavage and deprotection may be conducted with anhydrous amines (U.S. Pat. No. 5,750,672), methylamine (U.S. Pat. Nos. 5,348,868 and 5,518,651), hydrazine and ethanolamine (Polushin (1991) Nucleic Acids Res. Symposium Series No. 24, p. 49–50; Polushin (1994) Nucleic Acids Res. 22:639–45)

A typical post-synthesis, cleavage/deprotection routine on automated DNA synthesizers (e.g. Models 392, 394, 3948, Applied Biosystems, Foster City, Calif.) delivers concentrated ammonium hydroxide through the synthesis column after completion of oligonucleotide synthesis and allows it to stand in the column for about one hour, with periodic deliveries of more ammonium hydroxide and collection of the eluant in a vessel. The vessel containing the cleaved and partially deprotected oligo nucleotide can then be transferred to a heating device to complete deprotection. Alternatively, the nucleobase protecting groups may be sufficiently labile to not require further heating to yield a fully deprotected oligonucleotide. The ammonium hydroxide is removed under vacuum or in a stream of air or inert gas. The crude oligonucleotide may be purified by various methods, including hydrophobic cartridge purification, reverse-phase HPLC, polyacrylamide gel electrophoresis, and precipitation. For some applications, the crude oligonucleotide may be pure enough to perform adequately.

After completion of cleavage of the oligonucleotides from the support, the remaining protecting groups are removed by incubation in the ammonium hydroxide solution at either room temperature or with heating, e.g. 55° C. for 6–24 hours. Alternatively, oligonucleotides can be cleaved and/or deprotected with ammonia, or other amines, in the gas phase whereby the reagent gas comes into contact with the oligonucleotide while attached to, or in proximity to, the solid support (U.S. Pat. Nos. 5,514,789; 5,738,829).

The particular cleavage and deprotection protocol used in any situation is largely determined by protecting groups employed on the nucleobases, the internucleotide phosphorus, the sugars, 3' or 5' terminus, and any covalently attached label. The first generation set of nucleobase protecting groups utilized in the phosphodiester method of synthesis includes benzoyl (bz) and isobutyryl (ibu) protecting groups, utilized as adenosine $A^{bz}$, cytosine $C^{bz}$ and guanosine $G^{ibu}$ (Schaller (1963) J. Amer. Chem. Soc. 85, 3821–3827 and Buchi (1972) J. Mol. Biol. 72:251). Generally, thymidine T is not protected.

It is known that certain side-reactions occur during the cleavage and deprotection reactions. Modifications of the nucleobases, internucleotide phosphate groups, and pendant amino groups have been characterized (Chang (1999) Nucleosides & Nucleotides 18:1205–1206; Manoharan (1999) Nucleosides & Nucleotides 18:1199–1201). Acrylonitrile, released from deprotection of the internucleotide phosphate groups, may form adducts on the nucleobases, labels, or other sites (EP 1028124; WO 0046231; Eritja (1992) Tetrahedron 48:4171–82; Wilk (1999) J. Org. Chem. 64:7515–22). Other impurities are uncharacterized, but known to detract from the purity of oligonucleotides and cause loss of performance. Where deprotection of protecting groups is incomplete, oligonucleotides may hybridize with lower specificity or affinity, leading to mispriming or mutagenicity.

New reagents and methods for cleavage and deprotection of oligonucleotides are desirable. Certain protecting groups may not be compatible with deprotection reagents or automated synthesizers and protocols, leading to modifications. Certain labels, e.g. those with extended conjugation or reactive functionality, may lead to modifications of the labels or the oligonucleotide during the cleavage and deprotection steps. Reagents and methods which minimize or eliminate side reactions and modifications are desirable.

IV. SUMMARY

The present invention provides a process for the removal of protecting groups, i.e. deprotection, from chemically synthesized oligonucleotides. In one embodiment, the invention provides reagents suitable for use in such a process, and kits incorporating such reagents in a convenient, ready-to-use format. By use of the process and reagents of the invention, side-reactions leading to certain impurities that contaminate the synthesized oligonucleotides can be minimized.

In a first aspect, the invention provides a method for deprotection of an oligonucleotide by reacting a protected oligonucleotide with a deprotection reagent wherein the deprotection reagent comprises an active methylene compound and an amine reagent. The active methylene compound has the structure:

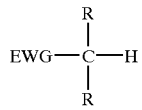

The substituent EWG is an electron-withdrawing group selected from nitro, ketone, ester, carboxylic acid, nitrile, sulfone, sulfonate, sulfoxide, phosphate, phosphonate, nitroxide, nitroso, trifluoromethyl and aryl groups substituted with one or more nitro, ketone, ester, carboxylic acid, nitrile, sulfone, sulfonate, sulfoxide, phosphate, phosphonate, nitroxide, nitroso, and trifluoromethyl. The substituent R is selected from hydrogen, $C_1$–$C_{12}$ alkyl, $C_6$–$C_{20}$ aryl, heterocycle and electron-withdrawing group. The amine reagent may be aqueous ammonium hydroxide, aqueous methylamine, or anhydrous $C_1$–$C_6$ alkylamine. In addition to an active methylene compound and an amine reagent, the deprotection reagent of the invention may include water or an alcohol solvent. Protecting groups are removed from the oligonucleotide by treatment with the deprotection reagent.

The oligonucleotide may be covalently attached to a solid support through a linkage. The oligonucleotide may be cleaved from the solid support either before, during, or after the protecting groups are removed. The solid support may be an organic polymer or inorganic. The solid support may be a membrane or frit which allows the deprotection reagent to pass through.

The solid support may be confined in a column or other enclosure which has inlet and outlet openings for the deprotection reagents to pass or flow through. The columns may be configured in a variety of formats, including holders of many columns, e.g. 96- or 384-well microtitre plate formats. A plurality of oligonucleotides in a holder may be deprotected concurrently or separately through discriminate or indiscriminate delivery or exposure to the deprotection reagents.

Oligonucleotides which may be deprotected by the deprotection reagents of the invention include nucleic acid analogs. Oligonucleotides may bear one or more covalently attached labels such as a fluorescent dye, a quencher, biotin, a mobility-modifier, and a minor groove binder.

In a second aspect, the invention provides a method for deprotection of an oligonucleotide by first wetting the protected oligonucleotide covalently attached to the solid support with an active methylene compound and a solvent, and then reacting the protected oligonucleotide with an amine reagent. The amine reagent may be in liquid or gas phase; aqueous or anhydrous, e.g. aqueous ammonium hydroxide, ammonia gas or a $C_1$–$C_6$ alkylamine.

In a third aspect, the invention includes an oligonucleotide deprotection reagent wherein the deprotection reagent comprises an active methylene compound and an amine reagent. The active methylene compound has the structure:

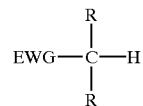

The substituent EWG is an electron-withdrawing group selected from nitro, ketone, ester, carboxylic acid, nitrile, sulfone, sulfonate, sulfoxide, phosphate, phosphonate, nitroxide, nitroso, trifluoromethyl and aryl groups substituted with one or more nitro, ketone, ester, carboxylic acid, nitrile, sulfone, sulfonate, sulfoxide, phosphate, phosphonate, nitroxide, nitroso, and trifluoromethyl. The substituent R is selected from hydrogen, $C_1$–$C_{12}$ alkyl, $C_6$–$C_{20}$ aryl, heterocycle and electron-withdrawing group. The active methylene compound may be 1 to 10% by volume of the deprotection reagent. The deprotection reagent may further include an alcohol solvent which is 1 to 30% by volume of the reagent.

In a fourth aspect, the invention includes deprotected oligonucleotides deprotected by the deprotectibn reagents of the invention.

V. BRIEF DESCRIPTION OF THE FIGURES

VI. DETAILED DESCRIPTION OF EXEMPLARY EMBODIMENTS

Figure 1A:
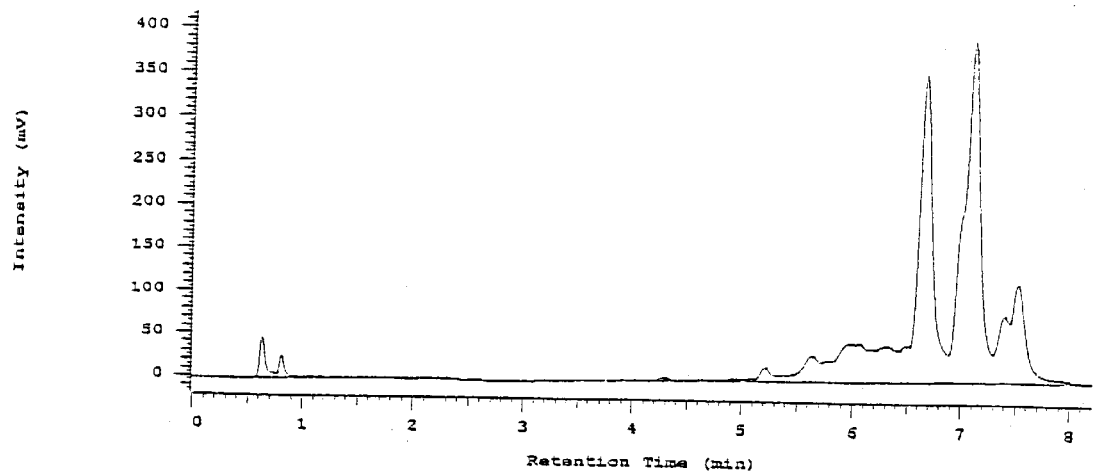
FIGS. 1a–1b show reverse-phase HPLC chromatograms of $T_{15}$-Q-CDPI$_3$, cleaved and deprotected with 15% ethanol:NH$_4$OH only (FIG. 1a) and with 3% diethylmalonate (DEM) in 15% ethanol:NH$_4$OH (FIG. 1b).

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

VI.1 DEFINITIONS

Unless stated otherwise, the following terms and phrases as used herein are intended to have the following meanings:

"Nucleobase" means a nitrogen-containing heterocyclic moiety capable of forming Watson-Crick hydrogen bonds in pairing with a complementary nucleobase or nucleobase analog, e.g. a purine, a 7-deazapurine, or a pyrimidine. Typical nucleobases are the naturally occurring nucleobases adenine, guanine, cytosine, uracil, thymine, and analogs of the naturally occurring nucleobases, e.g. 7-deazaadenine, 7-deazaguanine, 7-deaza-8-azaguanine, 7-deaza-8-azaadenine (U.S. Pat. No. 5,912,340), inosine, nebularine, nitropyrrole, nitroindole, 2-aminopurine, 2,6-diaminopurine, hypoxanthine, pseudouridine, pseudocytosine, pseudoisocytosine, 5-propynylcytosine, isoguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methyl-indole, phenoxazine, 7-deazapurine, pseudoisocytidine, isoguanosine, 4(3H)-pyrimidone, hypoxanthine, 8-oxopurines, pyrazolo[3,4-D]pyrimidines (U.S. Pat. Nos. 6,143,877 and 6,127,121) and ethenoadenine (Fasman (1989) *Practical Handbook of Biochemistry and Molecular Biology*, pp. 385–394, CRC Press, Boca Raton, Fla.).

"Nucleoside" means a compound consisting of a nucleobase linked to the C–1' carbon of a ribose sugar. The ribose may be substituted or unsubstituted. Substituted ribose sugars include, but are not limited to, those riboses in which one or more of the carbon atoms, e.g., the 2'-carbon atom, is substituted with one or more of the same or different —R, —OR, —NRR or halogen groups, where each R is independently hydrogen, $C_1$–$C_6$ alkyl or $C_5$–$C_{14}$ aryl. Sugars include ribose, 2'-deoxyribose, 2',3'-dideoxyribose, 2'-haloribose, 2'-fluororibose, 2'-chlororibose, 2'-C-alkyl, 2'-alkylribose, e.g. 2'-O-methyl, 4'-α-anomeric nucleotides, 1'-α-anomeric nucleotides, 2'-4'- and 3'-4'-linked and other "locked", bicyclic sugar modifications (WO 98/22489; WO 98/39352; WO 99/14226). Modifications at the 2'- or 3'-position include hydrogen, hydroxy, methoxy, ethoxy, allyloxy, isopropoxy, butoxy, isobutoxy, methoxyethyl, alkoxy, phenoxy, azido, amino, alkylamino, fluoro, chloro and bromo. When the nucleobase is purine, e.g. A or G, the ribose sugar is attached to the $N^9$-position of the nucleobase. When the nucleobase is pyrimidine, e.g. C, T or U, the pentose sugar is attached to the $N^1$-position of the nucleobase (Komberg and Baker, (1992) *DNA Replication*, $2^{nd}$ Ed., Freeman, San Francisco, Calif.).

"Nucleotide" means a phosphate ester of a nucleoside, as a monomer unit or within a nucleic acid. Nucleotides are sometimes denoted as "NTP", or "dNTP" and "ddNTP" to particularly point out the structural features of the ribose sugar. "Nucleotide 5'-triphosphate" refers to a nucleotide with a triphosphate ester group at the 5' position. The triphosphate ester group may include sulfur substitutions for the various oxygens, e.g. α-thio-nucleotide 5'-triphosphates.

As used herein, the terms "oligonucleotide" and "polynucleotide" are used interchangeably and mean single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, $Na^+$ and the like. A polynucleotide may be composed entirely of deoxyribonucleotides, entirely of ribonucleotides, or chimeric mixtures thereof. Polynucleotides may be comprised of internucleotide, nucleobase and sugar analogs. Polynucleotides typically range in size from a few monomeric units, e.g. 5–40, when they are frequently referred to as oligonucleotides, to several thousand monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine, unless otherwise noted.

"Protected oligonucleotide" means any oligonucleotide or polynucleotide prepared by synthesis means, e.g. phosphoramidite nucleoside method of automated synthesis on solid support, which includes one or more protecting groups on functional groups such as the exocyclic amine of a nucleobase, the internucleotide phosphate linkage, or 5' terminus hydroxyl or amine. Protecting group terminology follows the general strategies taught by Greene, T. and Wuts, P. "Protective Groups in Organic Synthesis", Third Edition, John Wiley & Sons, Inc., New York, N.Y. (1999).

The term "nucleic acid analogs" refers to analogs of nucleic acids comprising one or more nucleotide analog units, and possessing some of the qualities and properties associated with nucleic acids, e.g. Watson/Crick, wobble, and Hoogsteen base pairing, and other sequence recognition effects. Nucleic acid analogs may have modified nucleobase moieties, modified sugar moieties, and/or modified internucleotide linkages (Englisch (1991) Angew. Chem. Int. Ed. Engl. 30:613–29). Modifications include labels. One class of nucleic acid analogs is where the internucleotide moiety is modified to be neutral and uncharged at or near neutral pH, such as phosphoramidate, phosphotriester, and methyl phosphonate oligonucleotides where one of the nonbridging oxygen atoms is replaced by a neutral substituent, e.g. —$NR_2$, —OR, —R. Another class of nucleic acid analogs is where the sugar and internucleotide moieties have been replaced with an uncharged, neutral amide backbone, such as morpholino-carbamate and peptide nucleic acids (PNA). A form of PNA is a N-(2-aminoethyl)-glycine amide backbone polymer (Nielsen, 1991). Whenever a PNA sequence is represented, it is understood that the amino terminus is at the left side and the carboxyl terminus is at the right side.

"Deprotection reagent" means any reagent or formulation in a liquid or gaseous state which removes a protecting group from a protected oligonucleotide by chemical reaction, or cleaves an oligonucleotide from a solid support.

"Solid support" means any particle, bead, or surface upon which synthesis of an oligonucleotide occurs.

"Active methylene compound" means any organic reagent which bears an acidic proton bound to carbon and capable of removal under basic conditions, typically with a pKa of about 6 to 20.

The terms "cleaving" or "cleavage" refer to breaking a covalent bond that attaches an oligonucleotide to a solid support.

The term "label", as used herein, means any moiety which can be attached to an oligonucleotide and that functions to: (i) provide a detectable signal; (ii) interact with a second label to modify the detectable signal provided by the first or second label, e.g. FRET; (iii) stabilize hybridization, i.e. duplex formation; (iv) affect mobility, e.g. electrophoretic mobility or cell-permeability, by charge, hydrophobicity, shape, or other physical parameters, or (v) provide a capture moiety, e.g., affinity, antibody/antigen, or ionic complexation.

The terms "linker", "LINKER", and "linkage" are used interchangeably and mean a chemical moiety comprising a covalent bond or a chain of atoms that covalently attaches, or is attached to, a label to a polynucleotide, one label to another, or a solid support to a polynucleotide or nucleotide.

"Linking moiety" means a chemically reactive group, substituent or moiety, e.g. a nucleophile or electrophile, capable of reacting with another molecule to form a covalent bond, or linkage.

"Substituted" as used herein refers to a molecule wherein one or more hydrogen atoms are replaced with one or more non-hydrogen atoms, functional groups or moieties. For example, an unsubstituted nitrogen is —$NH_2$, while a substituted nitrogen is —$NHCH_3$. Exemplary substituents include but are not limited to halo, e.g., fluorine and chlorine, ($C_1$–$C_8$) alkyl, sulfate, sulfonate, sulfone, amino, ammonium, amido, nitrile, lower alkoxy, phenoxy, aromatic, phenyl, polycyclic aromatic, heterocycle, water-solubilizing group, and linking moiety.

"Alkyl" means a saturated or unsaturated, branched, straight-chain, branched, or cyclic hydrocarbon radical derived by the removal of one hydrogen atom from a single carbon atom of a parent alkane, alkene, or alkyne. Typical alkyl groups consist of 1–12 saturated and/or unsaturated carbons, including, but not limited to, methyl, ethyl, propyl, butyl, and the like.

"Alkoxy" means —OR where R is ($C_1$–$C_6$) alkyl.

"Alkyldiyl" means a saturated or unsaturated, branched, straight chain or cyclic hydrocarbon radical of 1–20 carbon atoms, and having two monovalent radical centers derived by the removal of two hydrogen atoms from the same or two different carbon atoms of a parent alkane, alkene or alkyne. Typical alkyldiyl radicals include, but are not limited to, 1,2-ethyldiyl, 1,3-propyldiyl, 1,4-butyldiyl, and the like.

"Aryl" means a monovalent aromatic hydrocarbon radical of 6–20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Aryldiyl" means an unsaturated cyclic or polycyclic hydrocarbon radical of 6–20 carbon atoms having a conjugated resonance electron system and at least two monovalent radical centers derived by the removal of two hydrogen atoms from two different carbon atoms of a parent aryl compound.

"Heterocycle" means any ring system having at least one non-carbon atom in a ring.

"Substituted alkyl", "substituted alkyldiyl", "substituted aryl" and "substituted aryldiyl" mean alkyl, alkyldiyl, aryl and aryldiyl respectively, in which one or more hydrogen atoms are each independently replaced with another substituent. Typical substituents include, but are not limited to, —X, —R, —OH, —OR, —SR, —SH, —$NH_2$, —NHR, —$NR_2$, —$^+NR_3$, —N=$NR_2$, —$CX_3$, —CN, —OCN, —SCN, —NCO, —NCS, —NO, —$NO_2$, —$N_2^+$, —$N_3$, —NHC(O)R, —C(O)R, —C(O)$NR_2$—S(O)$_2$O$^-$, —S(O)$_2$R, —OS(O)$_2$OR, —S(O)$_2$NR, —S(O)R, —OP(O)(OR)$_2$, —P(O)(OR)$_2$, —P(O)(O$^-$)$_2$, —P(O)(OH)$_2$, —C(O)R, —C(O)X, —C(S)R, —C(O)OR, —$CO_2^-$, —C(S)OR, —C(O)SR, —C(S)SR, —C(O)$NR_2$, —C(S)$NR_2$, —C(NR)$NR_2$, where each X is independently a halogen and each R is independently —H, $C_1$–$C_6$ alkyl, $C_5$–$C_{14}$ aryl, heterocycle, or linking group.

"Internucleotide analog" means a phosphate ester analog of an oligonucleotide such as: (i) alkylphosphonate, e.g. $C_1$–$C_4$ alkylphosphonate, especially methylphosphonate; (ii) phosphoramidate; (iii) alkylphosphotriester, e.g. $C_1$–$C_4$ alkylphosphotriester; (iv) phosphorothioate; and (v) phosphorodithioate. Internucleotide analogs also include non-phosphate analogs wherein the sugar/phosphate subunit is replaced by an a non-phosphate containing backbone structure. One type of non-phosphate oligonucleotide analogs has an amide linkage, such as a 2-aminoethylglycine unit, commonly referred to as PNA (Nielsen (1991) "Sequence-selective recognition of DNA by strand displacement with a thymidine-substituted polyamide", Science 254:1497–1500).

"Water solubilizing group" means a substituent which increases the solubility of the compounds of the invention in aqueous solution. Exemplary water-solubilizing groups include but are not limited to quaternary amine, sulfate, sulfonate, carboxylate, phosphonate, phosphate, polyether, polyhydroxyl, and boronate.

"Array" means a predetermined spatial arrangement of oligonucleotides present on a solid support or in an arrangement of vessels.

VI.2 OLIGONUCLEOTIDE SYNTHESIS

Oligonucleotides which are cleaved and deprotected by the reagents and methods of the invention may be synthesized on solid supports by the phosphoramidite method (U.S. Pat. Nos. 4,415,732 and 4,973,679; Beaucage, S. and Iyer, R. (1992) Tetrahedron 48:2223–2311) using: (1) 3' phosphoramidite nucleosides, I (2) supports e.g. silica, controlled-pore-glass (U.S. Pat. No. 4,458,066) and polystyrene (U.S. Pat. Nos. 5,047,524 and 5,262,530), and (3) automated synthesizers (Models 392, 394, 3948, 3900 DNA/RNA Synthesizers, Applied Biosystems). Other support materials include polyacrylate, hydroxethylmethacrylate, polyamide, polyethylene, polyethyleneoxy, or copolymers and grafts of such.

Generally, the phosphoramidite method of synthesis is preferred because of efficient and rapid coupling and the stability of the starting nucleoside monomers. The method entails cyclical addition of monomers, e.g. structure I, to an oligonucleotide chain growing on a solid-support, most commonly in the 3' to 5' direction in which the 3' terminus nucleoside is attached to the solid-support at the beginning of synthesis through a linkage. The linkage typically includes base-labile functionality, such as a succinate, diglycolate, oxalate, or hydroquinone-diacetate (Pon (1997) Nucleic Acids Res. 25:3629–35) and is cleavable by ammonia, amines, carbonate, hydroxide, and other basic reagents. The 3' phosphoramidite nucleoside monomer units are commercially available and share the general structure I:

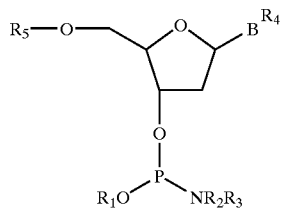

where, $R_1$ is a protecting group or substituent, e.g. 2-cyanoethyl, methyl, lower alkyl, substituted alkyl, phenyl, aryl, and substituted aryl; $R_2$ and $R_3$ are amine substituents, e.g. isopropyl, morpholino, methyl, ethyl, lower alkyl, cycloalkyl, and aryl; $R_4$ is an exocyclic nitrogen protecting group such as benzoyl, isobutyryl, acetyl, phenoxyacetyl, aryloxyacetyl, phthaloyl (U.S. Pat. No. 5,936,077), 2-(4-nitro-phenyl)ethyl, pent-4-enoyl, dimethylformamidine (dmf), dialkylformamidine, and dialkylacetamidine; and $R_5$ is an acid-labile protecting group such as 4,4'-dimethoxytrityl (DMT), 4-methoxytrityl (MMT), pixyl, trityl, and trialkylsilyl. Alternatively, oligonucleotides can be synthesized in the 5' to 3' direction with 5' phosphoramidite nucleoside monomers, e.g. the 5' bears a phosphoramidite group and the 3' bears an acid-labile protecting group (Wagner (1997) Nucleosides & Nucleotides, 16:1657–60).

Cleavage and deprotection with the reagents and methods of the invention may be conducted on oligonucleotides with more labile linkages to a solid support and more labile protecting groups. More labile nucleobase protecting groups are commercially available, e.g., phenoxyacetyl type: Expedite™ (Sinha (1993) Biochimie 75:13–23; available from Applied Biosystems, Foster City, Calif.) and PAC™ phosphoramidites (U.S. Pat. No. 4,980,460; Schulhof(1987) Nucleic Acids Res. 15:397–416; Schulhof(1988) Nucleic Acids Res. 16:319; available from Amersham Pharmacia), and formamidines and acetamidines (McBride (1986) J. Amer. Chem. Soc. 108:2040–48; Froehler (1983) Nucleic Acids Res. 11:8031–36; Theisen (1993) Nucleosides & Nucleotides 12:1033–46). These labile protecting groups are deprotected significantly faster than the first generation set. For example, the set $A^{bz}$, $C^{bz}$, $G^{dmf}$, T (Fastphoramidite™, Applied Biosystems, Foster City, Calif.) requires only one hour at 65° C. in concentrated ammonium hydroxide for complete deprotection.

The invention may be practiced on oligonucleotides which are covalently attached to any solid support through a linkage. The solid support may be any material, in any configuration, dimension, or scale upon which the oligonucleotide may be attached or synthesized. Typical solid supports include beads or particles of highly cross-linked polystyrene (U.S. Pat. Nos. 5,047,524; 5,262,530) or controlled-pore-glass. Dimensionally, solid supports may be approximately 1 to 100 μm average diameter and monodisperse or widely variant in size and shape. The beads or particles may be enclosed in a column having inlet and outlet openings. Reagents for conducting the phosphoramidite method of synthesis may be made to flow through a column mounted on the automated synthesizer. Alternatively, the solid support may be a porous membrane, filter, frit, or other flow-through device or configuration which conducts similar reagent flow.

Alternatively, the solid support may be an impermeable, rigid organic polymer, such as polyvinylchloride, polyethylene, polystyrene, polyacrylate, polycarbonate and copolymers thereof. Yet another solid support may be a non-porous, planar material such as glass, quartz, or diamond (EP 1063286). Suitable materials also include metals, e.g. aluminum, gold, platinum, silver, copper, and the like, or alloys thereof. The metals may be solid blocks, or surfaces, including layers. The materials may have at least one substantially planar surface in a slide, sheet, plate, or disc configuration (WO 01/01142). In one embodiment, a block material such as glass is coated with a metallic layer or thin film such as gold, silver, copper or platinum. Deposition of metal films may be conducted by methods such as electron beam evaporation. The metallic layer is derivatized with reactive functionality to which is attached an oligonucleotide. For example, a gold layer may be derivatized with a disulfide linkage to the 3' or 5' terminus of an oligonucleotide.

Inorganic solid supports such as glass, controlled-pore-glass, silica gel are typically derivatized with silane reagents such as aminoalkyl-trialkoxysilanes or mercaptoalkyl-trialkoxysilanes, which yield amino and thiol functional groups, respectively. Oligonucleotides, the initial nucleoside for oligonucleotide synthesis, or universal support reagents may then be covalently attached to the amino or thiol derivatized solid supports.

An array of solid support surfaces upon which oligonucleotides may be synthesized or attached may be made to undergo cleavage or deprotection with the reagents, and by the methods of the invention, in a parallel or sequential fashion. One or a subset of the protected oligonucleotides on an array may be selectively cleaved and deprotected by masking, targeted delivery of reagents, or other means of directing exposure to the reagents (Fodor, U.S. Pat. No. 5,445,934).

VI.3 METHODS OF OLIGONUCLEOTIDE CLEAVAGE AND DEPROTECTION

Upon completion of synthesis, the solid support-bound oligonucleotide is removed from the support by chemical cleavage of the covalent linkage between the oligonucleotide and the solid support, and deprotected to remove all remaining protecting groups from the oligonucleotide, including P from nucleobases and cyanoethyl from the internucleotide linkages. The steps of cleavage and deprotection may be coincidental and conducted with the same reagent, e.g. concentrated ammonium hydroxide when P is an amide type protecting group and LINKER is an ester, structure II. Alternatively, the steps of cleavage and deprotection can be conducted separately with "orthogonal" reagents. For example, when LINKER is disulfide, the nucleobase P and phosphate protecting groups may be removed from a protected oligonucleotide with ammonium hydroxide and the deprotected oligonucleotide will remain attached to the solid support. Conversely, the same protected oligonucleotide may be cleaved from the solid support with its protecting groups intact with a disulfide-selective cleaving reagent, such as dithithreitol. The net result of cleavage and deprotection is exemplified by the structures of a protected oligonucleotide II and a cleaved and deprotected oligonucleotide III:

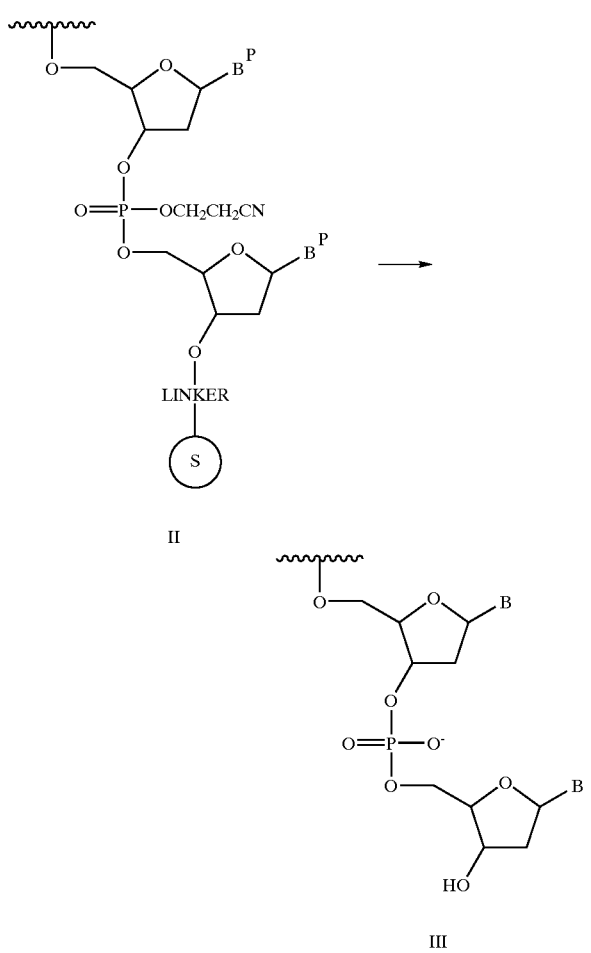

In one embodiment of the invention, the 3' terminus of a protected oligonucleotide is represented by structure II, showing 2 nucleotides of 5 to about 100 nucleotides. The nucleobases are protected with base-labile protecting groups, P. An exemplary set is $A^{bz}$, $G^{ibu}$, $C^{bz}$, and T. The internucleotide phosphate groups may be protected by 2-cyano ethyl, methyl, or some other protecting group. The 3' termninus is attached through a linkage, LINKER, to a solid support, S, in structure II. The linkage includes base-labile functionality such as ester, carbamate, or phosphate (EP 839 829). Typically the 3' ester is succinate, diglycolate, oxalate, or hydroquinone-diacetate. After synthesis, the protected oligonucleotide is reacted with a deprotection reagent of the invention to effect removal of nucleobase protecting groups, P, and internucleotide phosphate protecting groups, 2-cyanoethyl. Concurrently or separately, the 3' terminus linkage is cleaved to separate the oligonucleotide from the solid support to ultimately yield the cleaved and deprotected oligonucleotide shown by structure III.

In another embodiment, the linkage is chosen to be non-cleaving, i.e. resistant to cleavage during synthesis and deprotection steps. A non-cleaving linkage may contain inert types of functionality such as amide, alkyl, phosphate, or ether functionality. An oligonucleotide synthesized with a non-cleaving linkage may be deprotected by the reagents and methods of the invention and utilized in a solid-phase format, e.g. a biochip, DNA chip, or array, where a plurality of deprotected oligonucleotides are immobilized on a solid substrate. A grid or matrix of solid-support bound oligonucleotides may be thus arrayed in known locations and addressable by complementary nucleic acids or other reagents, light, a laser, current, or detection apparatus.

In another embodiment, the linkage to a solid support is chosen to be selectively cleavable, i.e. resistant to cleavage during synthesis and deprotection steps but cleavable with other reagents or conditions. A linkage to a solid support may be selectively cleavable when it contains a C—Si or an O—Si bond and cleavage is conducted with a fluoride anion reagent, e.g. tetra-butylammonium fluoride or triethylammonium hydrogen fluoride. A linkage may be selectively cleavable when it contains disulfide, —S—S—, functionality and is cleaved by dithiothreitol or other disulfide cleaving reagents. A linkage may be selectively cleavable when it contains an ortho-nitrobenzyl group and is cleaved under photolysis conditions.

A surprising and unexpected aspect of the invention is that a deprotection reagent including an active methylene compound and an amine reagent is effective and efficient at cleavage and deprotection of oligonucleotides. The novel deprotection reagents and methods of the invention may minimize undesired side reactions leading to impurities or modifications of oligonucleotides, including their covalently attached labels. The amine reagent serves as a nucleophile to displace the protecting groups and the active methylene compound serves to react with or render inert certain intermediates which may further react to modify the oligonucleotide or any label on the oligonucleotide. Other mechanisms may occur and other benefits may accrue from use of the deprotection reagent of the invention.

In one embodiment, the amine reagent and active methylene compound are mixed together to provide a deprotection reagent that can be applied to a protected oligonucleotide to remove protecting groups (Examples 1–3). The reaction may be conducted at room temperature or at an elevated temperature. When the protected oligonucleotide is covalently attached to a solid support through a linkage, the process of removing protecting groups may be concurrent with cleaving the oligonucleotide from the solid support. After cleavage, the cleaved oligonucleotide may be separated from the solid support by filtration through a flit or membrane, or by decantation. The cleaved oligonucleotide may be further deprotected under an elevated temperature or with addition of other reagents to assist in the removal of protecting groups. When deprotection is complete, the deprotected oligonucleotide may be separated from the deprotection reagents by conventional, well-known means such as evaporation, precipitation, electrophoresis, chromatography, or hydrophobic cartridge procedures. One or more of the compounds in the deprotection reagent may be sufficiently volatile to be removed by evaporation under a stream of gas or under vacuum.

The amine reagent may be used in a liquid formulation or in a gaseous state (Boal (1996) Nucleic Acids Res. 24:3115–17). Certain amines are gases at room temperature and pressure, such as ammonia (bp=−33° C.) and are effective at removing oligonucleotide protecting groups and conducting cleavage (Kempe, U.S. Pat. No. 5,514,789). The protected oligonucleotide may be contacted by ammonia gas in an enclosed, pressurized space, container, or bomb. The ammonia may be delivered through a conduit from a pressurized vessel as a gas (Kempe, U.S. Pat. No. 5,738,829), or generated from aqueous ammonium hydroxide within an enclosed space that also includes the protected oligonucleotide. In the latter embodiment, ammonia gas or a vapor of ammonia and water may be created by enclosure in an enclosed space of an open container, e.g. a pan or flask, of ammonium hydroxide solution. The gaseous state of the reagent increases in concentration by raising the temperature in the enclosed space (Example 6).

In another embodiment, the active methylene compound may contact the protected oligonucleotide prior to the amine reagent, or in a mixture including the amine reagent. In one embodiment, the active methylene compound and a solvent are mixed and used to wet a solid support to which a protected oligonucleotide is covalently attached. A sufficient volume of the mixture is delivered to cover the solid support or wet the surface, e.g. in a flow-through vessel such as a column (Example 6). The amine reagent is delivered next to the solid support, ensuring that a sufficient amount of the active methylene reagent is retained. The side-reaction suppression benefits of the active methylene reagent is thus realized by a sequential delivery of reagents.

VI.4 REAGENTS FOR OLIGONUCLEOTIDE CLEAVAGE AND DEPROTECTION

Oligonucleotides may be cleaved and/or deprotected by novel reagents of the invention which include an active methylene compound and an amine reagent. Active methylene compounds include organic reagents which bear an acidic proton bound to carbon capable of removal under basic conditions, typically with a pKa of about 6 to 20. The active methylene compound may constitute 1 to 10% by volume of the deprotection reagent. Active methylene compounds are represented by the structure:

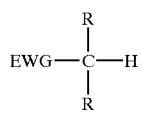

where the acidity of the carbon group is increased by an electron-withdrawing group (EWG). Other substituents (R) on the acidic carbon may be a second or third electron-withdrawing group, hydrogen, alkyl, aryl, or any functional group which renders the proton acidic in the range of about pKa=6–20. Electron-withdrawing groups include nitro, ketone, ester, carboxylic acid, nitrile, sulfone, sulfonate, sulfoxide, phosphate, phosphonate, nitroxide, nitroso, and trifluoromethyl. Electron-withdrawing groups also include aryl groups substituted with one or more nitro, ketone, ester, carboxylic acid, nitrile, sulfone, sulfonate, sulfoxide, phosphate, phosphonate, nitroxide, nitroso, and trifluoromethyl groups. Useful classes of active methylene compounds include: (i) 1,3 keto-esters, e.g. ethylacetoacetate; (ii) 1,3 diketones, e.g. 2,4-pentanedione and cyclohexanedione, (iii) malonate derivatives, e.g. malononitrile, malonic acid, malonamide, and dialkylmalonate diesters. Dialkylmalonate diesters include dimethylmalonate, diethylmalonate (DEM), di-n-propylmalonate, and diisopropylmalonate.

The effects of the concentration of an active methylene compound were investigated with four ethanolic ammonia (15% ethanol:conc. $NH_4OH$) reagents containing 0%, 0.1%, 1%, and 3% of diethylmalonate (FIGS. 2a–2d). Each of the four reagents was used to cleave and deprotect a portion of an oligonucleotide labelled with a fluorescent dye, a quencher moiety, and a minor groove binder (Example 3). Analysis by reverse phase HPLC showed significant contaminating impurities in the reagent without an active methylene compound (0% DEM). The presence of 0.1% DEM eliminated most of the impurities. The presence of 1% and 3% essentially eliminated all late eluting impurities.

In an embodiment where the active methylene compound is dissolved in a solvent and used to wet the solid support to which a protected oligonucleotide is covalently attached, prior to treatment with the amine reagent, the solvent may be selected from an alcohol, an ether, an amide, acetonitrile, dichloromethane, or dimethylsulfoxide. Alcohol solvents include methanol, ethanol, n-propanol, isopropanol, or 1,2-ethylene glycol. Ether solvents include diethyl ether, tetrahydrofuran, 1,4-dioxane, or 1,2-dimethoxyethane. Amide solvents include acetamide, formamide, benzamide, or dimethylformamide.

The amine reagent may be used in the gaseous state or dissolved in water, as a solution to treat the oligonucleotide on the solid support. The composition of the amine reagent includes any reagent with a primary, secondary, or tertiary amino group which reacts with a protected oligonucleotide to effect removal of the protecting groups. Amine reagents thus include: (i) ammonia ($NH_3$) gas; (ii) ammonia dissolved as ammonium hydroxide ($NH_4OH$) in water or mixtures of water and alcohol solvents; (iii) alkylamines, $R_2NH$ and $RNH_2$ where R is $C_1$–$C_6$ alkyl; (iv) alkyl and aryldiamines, $H_2N$—R—$NH_2$, where R is $C_1$–$C_{20}$ alkyldiyl or $C_6$–$C_{20}$ aryldiyl; and (v) formamidines such as 1,8-diazabicyclo[5.4.0]undec-7-ene (DBU) and 1,5-diazabicyclo[4.3.0]non-5-ene (DBN).

Alcohol solvents include methanol, ethanol, ethylene glycol, isopropanol, and other hydroxyl containing reagents which assist in solubilizing the reagents, wetting the solid support, increasing reaction rates, or minimizing side-reactions. The alcohol solvent may constitute 1 to 30% by volume of the deprotection reagent.

The amine reagent may contact the oligonucleotide in the gaseous state, generated from a solution in a closed system or environment with the oligonucleotide. For example, the protected oligonucleotide bound to a solid support may be enclosed in a container which further contains an open vessel of ammonium hydroxide solution. The container may be sealed, or open to the atmosphere. When sealed, the container may be heated, in the manner of a bomb apparatus. The ammonia vapors may thus contact the oligonucleotide and remove protecting groups. Alternatively, the amine reagent may be passed through, or delivered to, a column or it vessel containing the oligonucleotide. For example, the amine reagent may be installed on an automated synthesizer and delivered to a column, as part of the programmed delivery of reagents which may flow through the inlet and outlet openings of the column. The active methylene reagent may be delivered to the vessel containing the oligonucleotide prior to the amine reagent, or as a mixture with the amine reagent.

One or more columns in which the oligonucleotides are synthesized may be placed in, or transferred to, a holder apparatus, e.g. microtitre well tray, in which the method of deprotection of the invention may be conducted. The holder may be enclosed in a sealable vessel in which deprotection reagents are also placed or delivered. For example, a holder containing protected oligonucleotides on solid supports in columns can be sealed in a stainless steel pressure vessel. A deprotection reagent can either be placed in the vessel before sealing, or delivered through a conduit into the vessel. In this general manner, a plurality, e.g. several or hundreds, of oligonucleotides may be simultaneously cleaved and deprotected. Alternatively, more than one holder of columns may be sealed in the vessel. Also, the holders may be introduced and processed serially, by manual intervention, or programmed robotic means.

VI.5 LABELLED OLIGONUCLEOTIDES

Oligonucleotides to be cleaved and deprotected by the novel reagents and methods of the invention may be conjugated, "labelled" with label reagents. Such conjugates may find utility as DNA sequencing primers, PCR primers, oligonucleotide hybridization probes, oligonucleotide ligation probes, double-labelled 5'-exonuclease (TaqMan™) probes, size standards for electrophoresis, i.e. "lane standards" or "lane markers", and the like (U.S. Pat. No. 4,757,141; Andrus, "Chemical methods for 5' non-isotopic labelling of PCR probes and primers" (1995) in PCR 2: A Practical Approach, Oxford University Press, Oxford, pp. 39–54; Herrnanson, Bioconjugate Techniques, (1996) Academic Press, San Diego, Calif. pp. 40–55, 643–71; Mullah (1998) Nucl. Acids Res. 26:1026–1031).

Certain labels provide a signal for detection of the labelled oligonucleotide by fluorescence, chemiluminescence, or electrochemical luminescence (Kricka, L. in Nonisotopic DNA Probe Techniques (1992), Academic Press, San Diego, pp. 3–28). Fluorescent dyes useful for labelling oligonucleotides include fluoresceins, rhodamines (U.S. Pat. Nos. 5,366,860; 5,847,162; 5,936,087; 6,008,379; 6,191,278), energy-transfer dyes (U.S. Pat. Nos. 5,863,727; 5,800,996; 5,945,526), and cyanines (Kubista, WO 97/45539). Examples of fluorescein dyes include 6-carboxyfluorescein; 2',4',1,4,-tetrachlorofluorescein; and 2',4',5',7',1,4-hexachlorofluorescein (Menchen, U.S. Pat. No. 5,118,934). Fluorescence has largely supplanted radioactivity as the preferred detection method for many ligation experiments and applications, such as the oligonucleotide ligation assay and other in vitro DNA probe-based diagnostic tests.

Another class of labels includes fluorescence quenchers. The emission spectra of a quencher overlaps with a proximal intramolecular or intermolecular fluorescent dye such that the fluorescence of the fluorescent dye is substantially diminished, or quenched, by the phenomenon of fluorescence resonance energy transfer "FRET" (Clegg (1992) "Fluorescence resonance energy transfer and nucleic acids", Meth. Enzymol. 211:353–388). An example of FRET in the present invention is where the oligonucleotide is labelled with a fluorescent dye and a fluorescence quencher. Particular quenchers include but are not limited to (i) rhodamine dyes selected from the group consisting of tetramethyl-6-carboxyrhodamine (TAMRA), tetrapropano-6-carboxyrhodamine (ROX); (ii) diazo compounds, e.g. DABSYL, DABCYL (Matayoshi (1990) Science 247:954–58; Tyagi, WO 95/13399), Fast Black, (Nardone, U.S. Pat. No. 6,117,986); (iii) cyanine dyes (Lee, U.S. Pat. No. 6,080,868) and, (iv) other chromophores e.g. anthraquinone, malachite green, nitrothiazole, and nitroimidazole compounds and the like.

Energy-transfer dyes are another type of oligonucleotide label. An energy-transfer dye label includes a donor dye linked to an acceptor dye (U.S. Pat. No. 5,800,996). Light, e.g. from a laser, at a first wavelength is absorbed by a donor dye, e.g. FAM. The donor dye emits excitation energy absorbed by the acceptor dye. The acceptor dye fluoresces at a second, longer wavelength. The donor dye and acceptor dye moieties of an energy-transfer label may be attached by a linkage linking the 4' or 5' positions of the donor dye, e.g. FAM, and a 5- or 6-carboxyl group of the acceptor dye. Other rigid and non-rigid linkages may be useful.

Metal porphyrin complexes, e.g. aluminum phthalocyanine tetrasulfonate (Stanton, WO 88/04777) and chemiluminescent compounds, e.g. 1,2-dioxetane chemiluminescent moieties (Bronstein, U.S. Pat. No. 4,931,223) are other examples of useful oligonucleotide labels.

Another class of labels, referred to herein as hybridization-stabilizing moieties, include but are not limited to minor groove binders (Blackburn, M. and Gait, M. Nucleic Acids in Chemistry and Biology (1996) Oxford University Press, p. 337–46), intercalators, polycations, such as poly-lysine and spermine, and cross-linking functional groups. Hybridization-stabilizing moieties may increase the stability of base-pairing, i.e. affinity, or the rate of hybridization, exemplified by high thermal melting temperatures, Tm, of the duplex. Hybridization-stabilizing moieties may also increase the specificity of base-pairing, exemplified by large differences in Tm between perfectly complementary oligonucleotide and target sequences and where the resulting duplex contains one or more mismatches of Watson/Crick base-pairing (Blackburn, M. and Gait, M. Nucleic Acids in Chemistry and Biology (1996) Oxford University Press, pp. 15–81). Labels which enhance hybridization specificity and affinity are desirable, e.g. minor-groove binders and affinity ligand labels. Biotin and digoxigenin are useful affinity ligand labels for the capture and isolation of oligonucleotides. Minor groove binders include Hoechst 33258, $CDPI_{1-3}$ (U.S. Pat. No. 6,084,102; WO 96/32496; Kutyavin (2000) Nucleic Acids Res. 28:655–61), netropsin, and distamycin. Other useful labels include electrophoretic mobility modifiers, amino acids, peptides, and enzymes.

A labelled oligonucleotide may have formula IV:

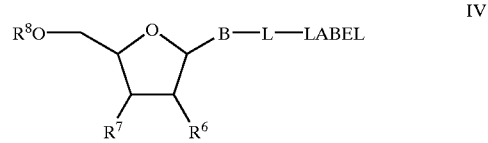

IV where the oligonucleotide comprises 2 to 1000 nucleotides. LABEL is a protected or unprotected form of a fluorescent dye, an exemplary class of labels, which includes an energy-transfer dye. B is any nucleobase, e.g. uracil, thymine, cytosine, adenine, 7-deazaadenine, guanine, and 8-deazaguanosine. L is a linkage, such as a propargyl amine (U.S. Pat. Nos. 5,047,519; 5,770,716; 5,821,356; 5,948,648). $R^6$ is H, OH, halide, azide, amine, $C_1$–$C_6$ aminoalkyl, $C_1$–$C_6$ alkyl, allyl, protected hydroxyl, trialkylsilyloxy, tert-butyldimethylsilyloxy, $C_1$–$C_6$ alkoxy, $OCH_3$, or $OCH_2CH{=}CH_2$. $R^7$ is H, phosphate, internucleotide phosphodiester, or internucleotide analog. $R^8$ is H, phosphate, internucleotide phosphodiester, or internucleotide analog. In this embodiment, the nucleobase-labelled oligonucleotide IV may bear multiple labels attached through the nucleobases. Nucleobase-labelled oligonucleotide IV may be formed by: (i) coupling of a nucleoside phosphoramidite reagent by automated synthesis or (ii) post-synthesis coupling with a label reagent. Oligonucleotides labelled at the 5' terminus have structure V:

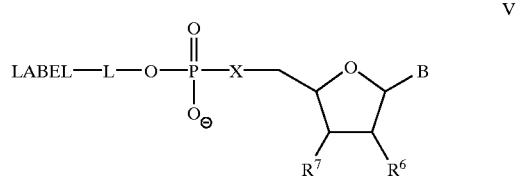

V where X is O, NH, or S; $R^6$ is H, OH, halide, azide, amine, $C_1$–$C_6$ aminoalkyl, $C_1$–$C_6$ alkyl, allyl, $C_1$–$C_6$ alkoxy, $-OCH_3$, or $-OCH_2CH{=}CH_2$; $R^7$ is H, phosphate, internucleotide phosphodiester, or internucleotide analog; and L is $C_1$–$C_{12}$ alkyldiyl, $C_6$–$C_{20}$ aryldiyl, or polyethyleneoxy of up to 100 ethyleneoxy units.

A variety of labels may be covalently attached at the 3' terminus of oligonucleotides. A solid support bearing a label, or bearing functionality which can be labelled by a post-synthesis reaction, can be utilized as a solid support for oligonucleotide synthesis (U.S. Pat. Nos. 5,141,813; 5,231,191, 5,401,837; 5,736,626). By this approach, the label or the functionality is present during synthesis of the oligonucleotide. During cleavage and deprotection, the label or the functionality remains covalently attached to the oligonucleotide. Oligonucleotides labelled at the 3' terminus may have structure VI:

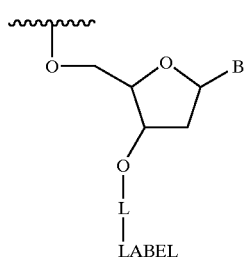

VI

The linkage L in formulas IV, V, VI may be attached at any site on the label, LABEL.

Labelling can be accomplished using any one of a large number of known techniques employing known labels, linkages, linking groups, standard reagents and reaction conditions, and analysis and purification methods. Generally, the linkage linking the label and the oligonucleotide should not (i) interfere with hybridization, (ii) inhibit enzymatic activity, or (iii) adversely affect the properties of the label, e.g. quenching or bleaching fluorescence of a dye. Oligonucleotides can be labelled at sites including a nucleobase, a sugar, an internucleotide linkage, and the 5' and 3' terminii. Oligonucleotides can be functionalized to bear reactive amino, thiol, sulfide, disulfide, hydroxyl, and carboxyl groups at any of these sites. Nucleobase label sites generally include the 7-deaza or C-8 positions of the purine or deazapurine, and the C-5 position of the pyrimidine. The linkage between the label and the nucleobase may be acetylenic-amido or alkenic-amido linkages. Typically, a carboxyl group on the label is activated by forming an active ester, e.g. N-hydroxysuccinimide (NHS) ester and reacted with an amino group on the alkynylamino- or alkenylamino-derivatized nucleobase. Labels are most conveniently and efficiently introduced at the 5' terminus (Andrus, A. "Chemical methods for 5' non-isotopic labelling of PCR probes and primers" (1995) in PCR 2: A Practical Approach, Oxford University Press, Oxford, pp. 39–54) with fluorescent dyes and other labels which have been functionalized as phosphoramidite reagents, as part of the automated protocol.

Oligonucleotides may be labelled at both the 5' and 3' terminii. Each terminii may bear one or more labels. For example, Examples 1–4 include oligonucleotides with a 5' fluorescent dye and two labels, a quencher Q and a minor groove binder CDPI$_3$, at the 3' terminus.

In a first method for labelling synthetic oligonucleotides, a nucleophilic functionality, e.g. a primary aliphatic amine, is introduced at a labelling attachment site on an oligonucleotide, e.g. a 5' terminus. After automated, solid-support synthesis is complete, the oligonucleotide is cleaved from the support and all protecting groups are removed. The nucleophile-oligonucleotide is reacted with an excess of a label reagent containing an electrophilic moiety, e.g. isothiocyanate or activated ester, e.g. N-hydroxysuccinimide (NHS), under homogeneous solution conditions (Hermanson, Bioconjugate Techniques, (1996) Academic Press, San Diego, Calif. pp. 40–55, 643–71; Andrus, A. "Chemical methods for 5' non-isotopic labelling of PCR probes and primers" (1995) in PCR 2: A Practical Approach, Oxford University Press, Oxford, pp. 39–54). Labelled oligonucleotides IV, V, or VI may be formed by reacting a reactive linking group form , e.g. NHS, of a dye, with an oligonucleotide functionalized with an amino, thiol, or other nucleophile (U.S. Pat. No. 4,757,141).

In a second method, a label is directly incorporated into the oligonucleotide during or prior to automated synthesis, for example as a support reagent (U.S. Pat. Nos. 5,736,626 and 5,141,813) or as a non-nucleoside phosphoramidite reagent. Certain fluorescent dyes and other labels have been functionalized as phosphoramidite reagents for 5' labelling (Theisen (1992) Nucleic Acid Symposium Series No. 27, Oxford University Press, Oxford, pp. 99–100).

Polynucleotides may be labelled with moieties that affect the rate of electrophoretic migration, i.e. mobility-modifying labels. Mobility-modifying labels include polyethyleneoxy units, —(CH$_2$CH$_2$O)$_n$— where n may be 1 to 100 (U.S. Pat. No. 5,624,800). The polyethyleneoxy units may be interspersed with phosphate groups. Specifically labelling polynucleotides with labels of polyethyleneoxy of discrete and known size allows for separation by electrophoresis, substantially independent of the number of nucleotides in the polynucleotide. That is, polynucleotides of the same length may be discriminated upon by the presence of spectrally resolvable dye labels and mobility-modifying labels. Polynucleotides bearing both dye labels and mobility-modifying labels may be formed enzymatically by ligation or polymerase extension of the single-labelled polynucleotide or nucleotide constituents.

The present invention is particularly well suited for cleaving and deprotecting polynucleotides with multiple and different labels.

VI.6 EXAMPLES

The invention will be further clarified by a consideration of the following examples, which are intended to be purely exemplary of the invention and not to in any way limit its scope.

Example 1

An oligonucleotide T$_8$-Q-CDPI$_3$:

5' TTT TTT TT-Q-CDPI$_3$ 3' (SEQ ID. NO. 1)

was synthesized on the Model 3948 DNA Synthesizer (Applied Biosystems, Foster City, Calif.). Eight cycles of phosphoramidite chemistry was conducted with thymidine 3' phosphoramidite in a column containing 16 mg (200 nmoles) highly cross-linked polystyrene bead support loaded with 12 μmole/gm of a linkage including quencher label Q and minor groove binder label CDPI$_3$. The quencher label, Q, has the structure:

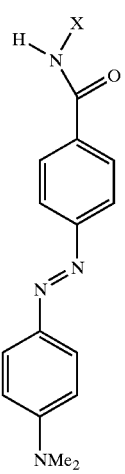

where X is the attachment site to a linkage. The minor-groove-binder label, CDPI₃, has the following structure:

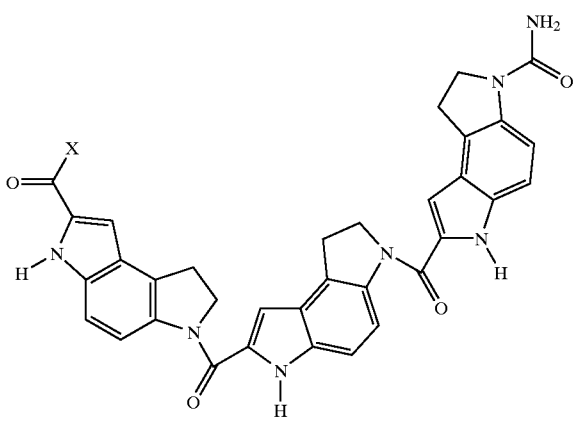

where X is the attachment site to a linkage.

The support was divided into two portions. The first portion was treated with 15% ethanolic ammonia (15:85 v/v EtOH:conc. NH₄OH) for 2 hours at 55° C. to effect cleavage and deprotection. The second portion was treated with 3% diethylmalonate (DEM) dissolved in 15% ethanolic ammonia (3:15:82 v/v/v DEM:EtOH:conc. NH₄OH), for 2 hours at 55° C.

After cooling, an aliquot from each portion was analyzed by reverse phase HPLC. The adsorbent was 2–5 μm particles of C-18 polystyrene/divinylbenzene. The mobile phases were a gradient of acetonitrile in TEAA (triethylammonium acetate) at about pH 7. (Transgenomic WAVE, Transgenomic, Inc., San Jose, Calif.). Other mobile phases, conditions, and HPLC equipment are also useful for analyzing the oligonucleotides which are cleaved and deprotected by the methods and reagents of the invention. The major, product peak and the major (first) late-eluting contaminant were separated and isolated from each aliquot. The late-eluting contaminant(s) from the first portion, cleaved and deprotected without DEM, were analyzed by MALDI-TOF mass spectrometry (PerSeptive Biosystems Voyager-DE, Framingham, Mass.) and found to have a mass of 3485.5 [M+26] mass units. This mass is consistent with an additional vinyl group modification (—CH₂=CH₂). The major peak in the HPLC from each portion was assigned to T₈-Q-CDPI₃ from the strong molecular ion peak at 3459.41 mass units (positive mode), as expected.

Example 2

Figure 1B:
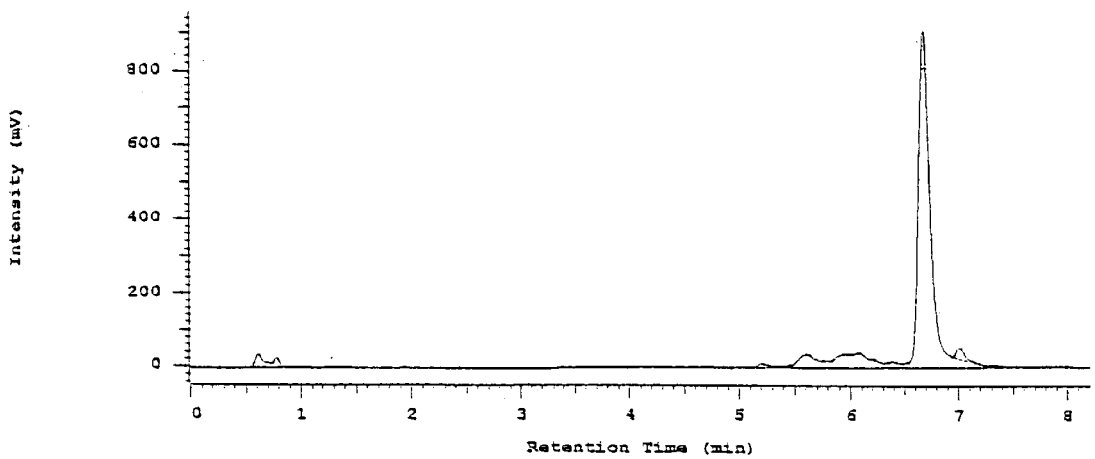
Figure 2A:
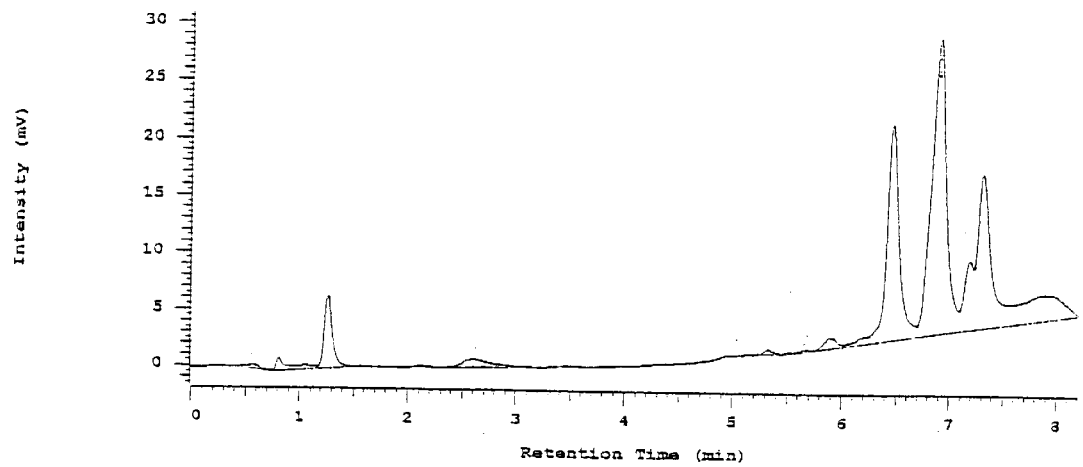
FIGS. 2a–2d show reverse-phase HPLC chromatograms of 5' F-CAG TCG CCC TGC C-Q-CDPI$_3$ 3' (SEQ ID. NO 3) cleaved and deprotected with 15% ethanol:NH4OH and either 0% DEM (FIG. 2a), 0.1% DEM (FIG. 2b), 1% DEM (FIG. 2c), or 3% DEM (FIG. 2d).
Figure 2B:
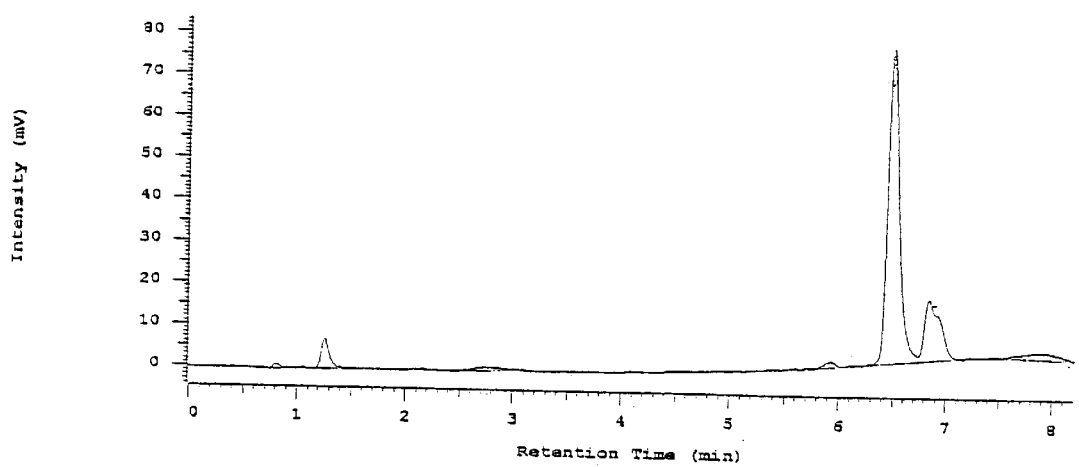
Figure 2C:
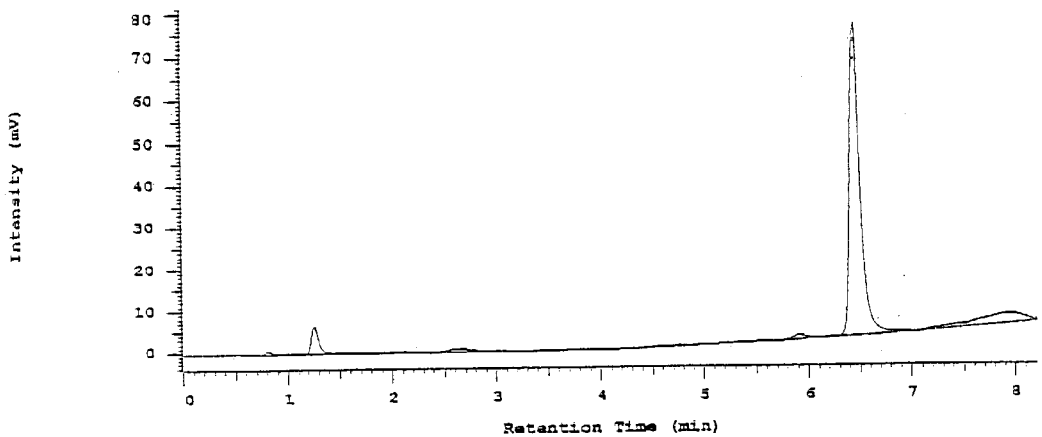
Figure 2D:
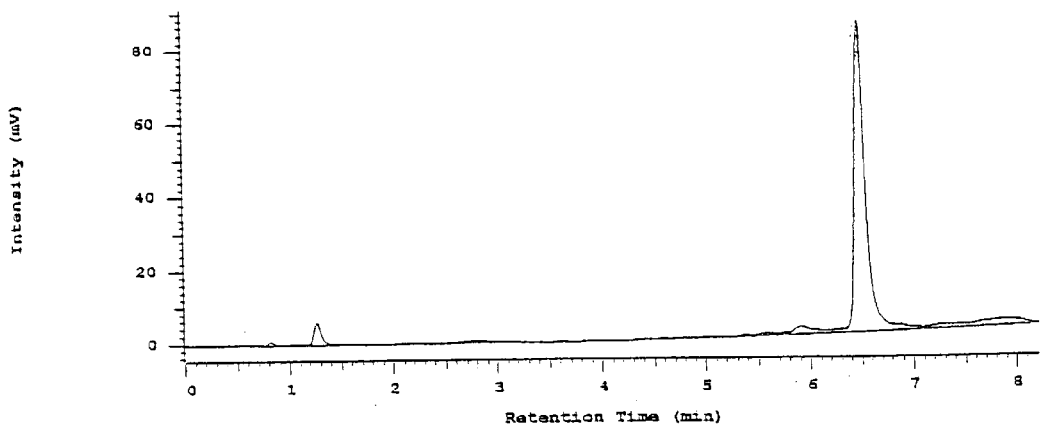

An oligonucleotide T₁₅-Q-CDPI₃:

5' TTT TTT TTT TTT TTT-Q-CDPI₃ 3' (SEQ ID. NO. 2) was synthesized on the Model 3948 DNA Synthesizer (Applied Biosystems, Foster City, Calif.). Fifteen cycles of phosphoramidite chemistry was conducted with thymidine 3' phosphoramidite in a column containing 16 mg (200 nmoles) highly cross-linked polystyrene bead support loaded with 12 μmole/gm of a linkage including quencher label Q and minor groove binder label CDPI₃. The support was divided into two portions. The first portion was treated with 15% ethanolic ammonia (15:85 v/v EtOH:conc. NH₄OH) for 2 hours at 55° C. to effect cleavage and deprotection. The second portion was treated with 3% diethylmalonate (DEM) dissolved in 15% ethanolic ammonia (3:15:82 v/v/v DEM:EtOH:conc. NH₄OH), for 2 hours at 55° C. After cooling, an aliquot from each portion was analyzed by reverse phase HPLC. The portion cleaved and deprotected without DEM shows a complex product mixture containing only 26.5% of the desired product eluting at 6.1 minutes (FIG. 1a). The product mixture is contaminated with significant (50%) later eluting impurities. The portion cleaved and deprotected with 3% DEM shows improved purity, 76.8% of the desired product eluting at 6.1 minutes and a diminished level of later eluting impurities (FIG. 1b).

Example 3

Oligonucleotides labelled with a fluorescent dye (F=6-carboxyfluorescein) at the 5' terminus, and a quencher moiety (Q) and minor groove binder (CDPI₃) at the 3' terminus:

5' F-CAG TCG CCC TGC C-Q-CDPI₃ 3'   (SEQ ID. NO. 3)

5' F-CTT CTT GCT AAT TCC-Q-CDPI₃ 3' (SEQ ID. NO. 4)

were synthesized on a Model 3900 DNA Synthesizer (Applied Biosystems, Foster City, Calif.). Phosphoramidite chemistry was conducted with nucleoside 3' phosphoramidites, including $A^{bz}$, $G^{dmf}$, $C^{bz}$ and T, in a column containing 16 mg (200 nmoles) highly cross-linked polystyrene bead support loaded with 12 μmole/gm of a linkage including quencher label Q and minor groove binder label CDPI₃.

After each synthesis, the support was divided into four portions. Each portion was treated with a reagent containing 0%, 0.1%, 1% or 3% diethylmalonate (DEM) in 15% ethanolic ammonia (15:85 v/v EtOH:conc. NH₄OH) for 2 hours at 65° C. to effect cleavage and deprotection.

Figure 3A:
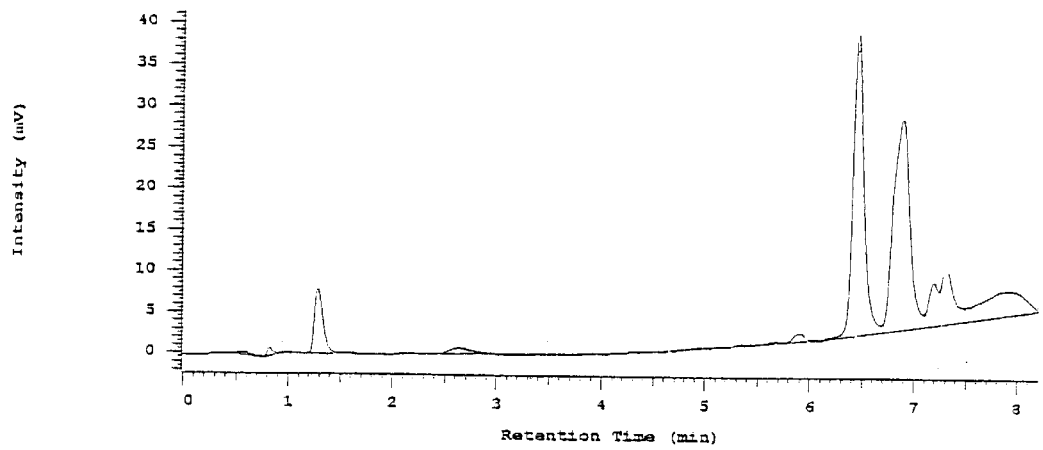
FIGS. 3a–3d show reverse-phase HPLC chromatograms of 5' F-CTT CTT GCT AAT TCC-Q-CDPI$_3$ 3' (SEQ ID. NO 4) cleaved and deprotected with 15% ethanol:NH4OH and either 0% DEM (FIG. 3a), 0.1% DEM (FIG. 3b), 1% DEM (FIG. 3c), or 3% DEM (FIG. 3d).
Figure 3B:
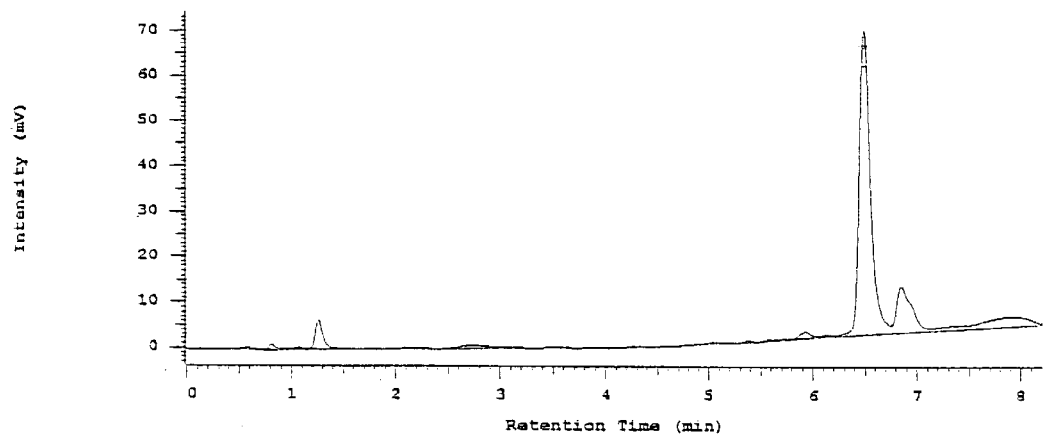
Figure 3C:
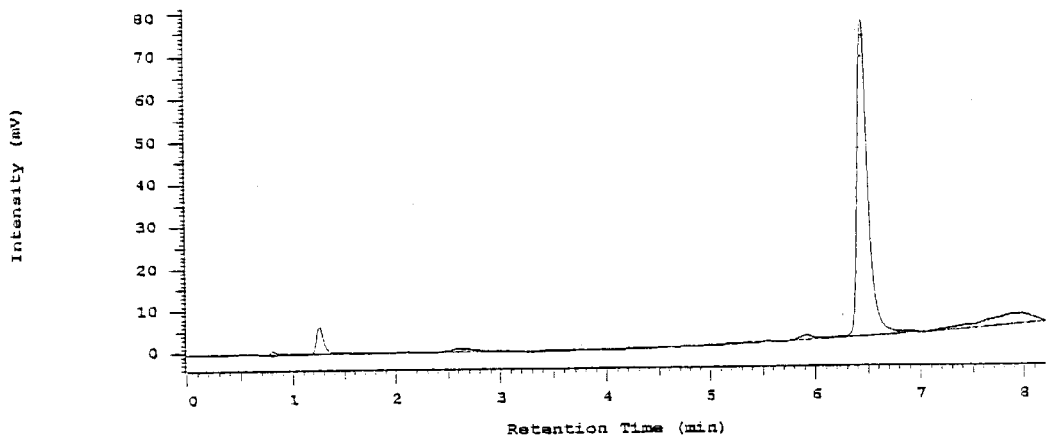
Figure 3D:
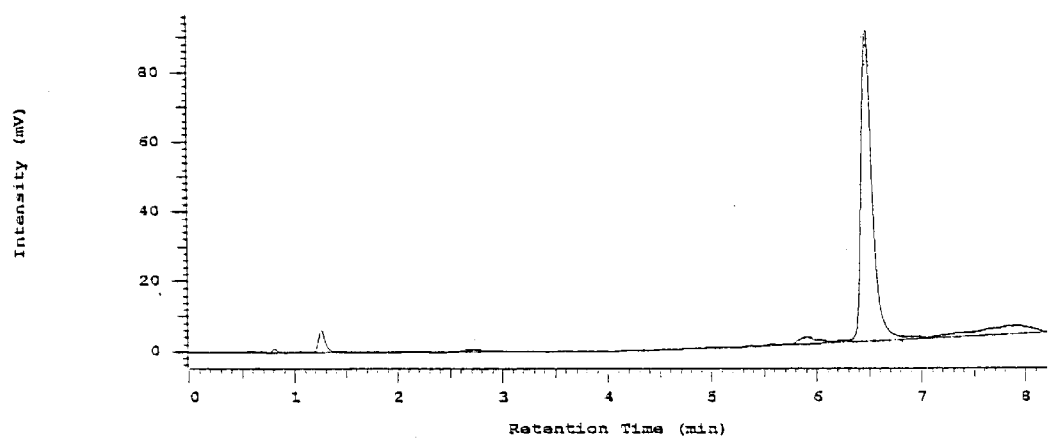

After cooling, an aliquot from each portion was analyzed by reverse phase HPLC. The portions cleaved and deprotected without DEM shows a complex product mixture containing only 21.8% of the desired product eluting at 6.5 minutes (FIG. 2a) and 32.7% of the desired product eluting at 6.4 minutes (FIG. 3a) for SEQ ID. NO 3 and SEQ ID. NO 4 respectively. The product mixtures are contaminated with significant (50%) later eluting impurities. The portions cleaved and deprotected with 0.1% DEM show improved purities; 65.8% (FIG. 2b) and 64.4% (FIG. 3b) and diminished levels of later eluting impurities for SEQ ID. NO 3 and SEQ ID. NO 4 respectively. The portions cleaved and deprotected with 1% DEM show again improved purities; 76.7% (FIG. 2c) and 76.7% (FIG. 3c) for SEQ ID. NO 3 and SEQ ID. NO 4 respectively. The portions cleaved and deprotected with 3% DEM show again improved purities, 79.5% (FIG. 2d) and 77.5% (FIG. 3d) for SEQ ID. NO 3 and SEQ ID. NO 4 respectively.

The fluorescent dye, 6-carboxyfluorescein, (F) has the following structure:

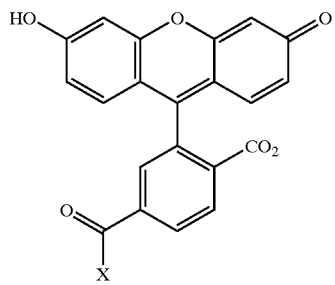

where X is the attachment site to a linkage.

Example 4

Figure 4A:
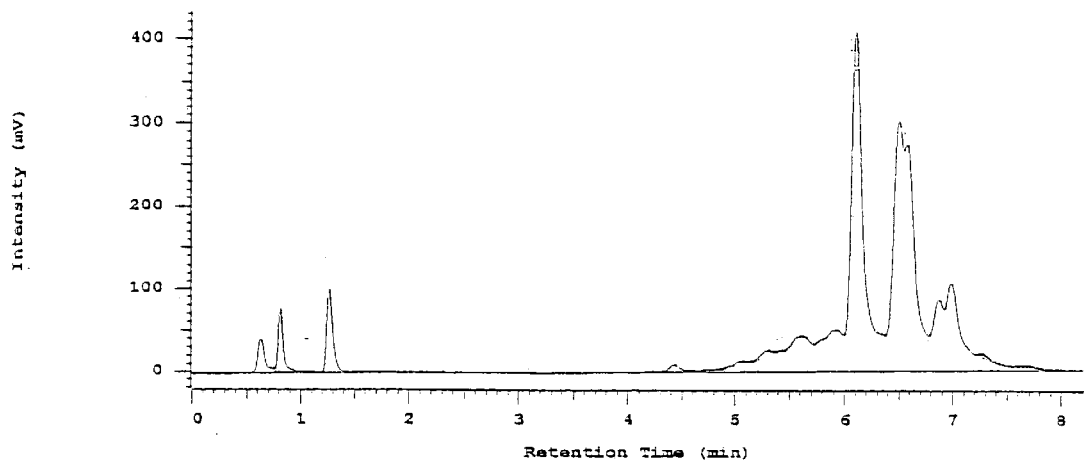
FIGS. 4a–4b show reverse-phase HPLC chromatograms of 5' F-CCA TGC GTT AGC C-Q-CDPI$_3$ 3' (SEQ ID. NO. 5) cleaved and deprotected with 15% ethanol:NH$_4$OH only (FIG. 4a) and with 3% diethylmalonate (DEM) in 15% ethanol:NH$_4$OH (FIG. 4b).
Figure 4B:
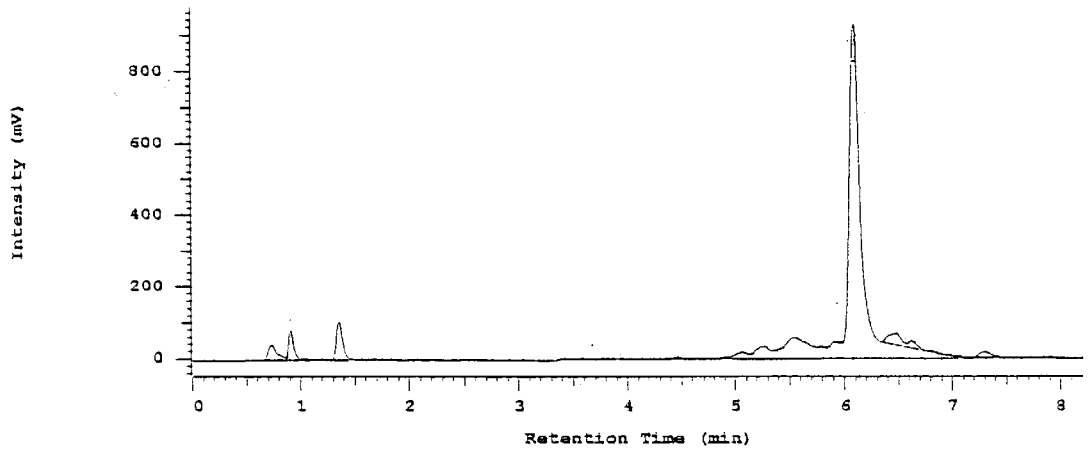

Following the procedures of Example 3, the 13 nt oligonucleotide:

5' F-CCA TGC GTT AGC C-Q-CDPI$_3$ 3' (SEQ ID. NO. 5)

was synthesized and the support was divided into two portions. One portion was cleaved and deprotected with 15% ethanol:NH$_4$OH only and with 3% DEM in 15% ethanol:NH$_4$OH. An aliquot from each portion was analyzed by reverse phase HPLC. The portion cleaved and deprotected without DEM shows a complex product mixture containing only 26% of the desired product eluting at 6.1 minutes (FIG. 4a). The product mixture is contaminated with significant later eluting impurities. The portion cleaved and deprotected with 3% DEM shows improved purity, 67% of the desired product eluting at 6.1 minutes and a diminished level of later eluting impurities (FIG. 4b).

Example 5

Liquid phase cleavage/deprotection:

A set of up to 48 oligonucleotides are synthesized on the Model 3948 DNA Synthesizer (Applied Biosystems, Foster City, Calif.). Each oligonucleotide is synthesized at 50–100 nmolar scale on about 20 mg of 3' nucleoside, high-crosslink polystyrene in a OneStep™ synthesis/purification column (Applied Biosystems, Foster City, Calif.; Andrus, U.S. Pat. Nos. 5,935,527 and 6,175,006; Baier (1996) BioTechniques 20:298–303). Oligonucleotides may be 15–50 nt, or longer. Oligonucleotides may be unlabelled or labelled with labels such as fluorescent dyes or hybridization-stabilizing moieties. Synthesis is conducted with the Fastphoramidlte™ set of 3' phosphoramidite nucleosides (A$^{bz}$, G$^{dmf}$, C$^{bz}$, T) dissolved in acetonitrile and coupled to the 5' terminus of the growing oligonucleotide with tetrazole, or a tetrazole analog, e.g. 5-ethylthiotetrazole, as a proton-source activator. Synthesis may be programmed to either remove the 5' DMT group from the 5' terminus of the oligonucleotide by acidic detritylation, or leave it intact by omitting the final detritylation step. When a set of three oligonucleotides finishes the synthesis stage under the synthesis fluid delivery head, the set of three columns rotates under the cleavage/deprotection delivery head. The deprotection reagent of the invention may be delivered to the columns, e.g. 0.5 to 1.5 ml of a mixture of concentrated ammonium hydroxide and an active methylene compound. The active methylene compound may be 1 to 10% by volume of the reagent. The deprotection reagent may further contain 1 to 30% of an alcohol solvent, by volume. The deprotection reagent is allowed to stand in, or circulate through, the column at ambient or higher temperature for several minutes to an hour. The oligonucleotide is thereby cleaved from the solid support and can be delivered to enclosed tubing which is heated at about 65° C. for about 1–2 hours to complete deprotection, i.e. removal of nucleobase and internucleotide protecting groups.

When the 5' DMT group has been left intact, the solution containing the deprotected oligonucleotide may be purified by trityl-selective hydrophobic interaction by absorption onto the polystyrene in the OneStep column in which it was synthesized. Following absorption (loading), the column is treated with reagents to effect washing away of impurities, detritylation of the oligonucleotide, and elution of the deprotected, purified, and detritylated oligonucleotide.

Example 6

Gas phase cleavage/deprotection:

A set of 48 oligonucleotides were synthesized in a single pre-programmed run on the Model 3900 DNA Synthesizer (Applied Biosystems, Foster City, Calif.). Each oligonucleotide was synthesized at a 200 nmolar scale on about 10 mg of polystyrene support in a column with inlet and outlet openings. The oligonucleotides ranged in size from 15 to 30 nt in length. After synthesis of the 48 oligonucleotides was complete, 200 µl of a 1% DEM in acetonitrile solution was delivered to each column. Argon gas was flushed through the openings for about 30 seconds to expel most of the solution. The columns were then transferred to a holder, e.g. 96 well microtiter format. The holder was placed in a sealable stainless steel, pressure vessel with an internal volume of approximately one gallon. Up to four such holders could be placed in the vessel for parallel cleavage and deprotection operations. The holders were placed on a mesh screen affixed approximately 1 inch from the bottom of the vessel. Approximately 450 ml of chilled, concentrated ammonium hydroxide solution was added to the bottom floor of the vessel, or into a shallow pan that sits on the bottom floor of the vessel, below the mesh screen. The columns or holders were not in direct contact with the ammonium hydroxide solution. The vessel was sealed and heated to 65° C. for about 2 hours. The pressure generated inside during the heating period was about 45 psi. The vessel was cooled, vented, and opened.

The holders containing the columns were removed from the vessel and placed in a device whereby a vacuum can be applied to draw liquids and air through the inlet opening of the columns. To each column, 250 µl of water was delivered and pulled through to waste. The cleaved and deprotected oligonucleotides were eluted by delivering 250 µl of 20% (50% for labelled oligonucleotides) acetonitrile in water to each column and collecting the eluant in a vessel mounted below the outlet opening of the column. Alternatively, the liquid reagents, i.e. water wash or eluant solution, can be drawn through the column by centrifugation where the holder is rotated in a centrifuge. The eluted oligonucleotides can be dried under vacuum and resuspended in an aqueous medium, further diluted, or used directly by aliquot in experiments.

Example 7

Figure 5A:
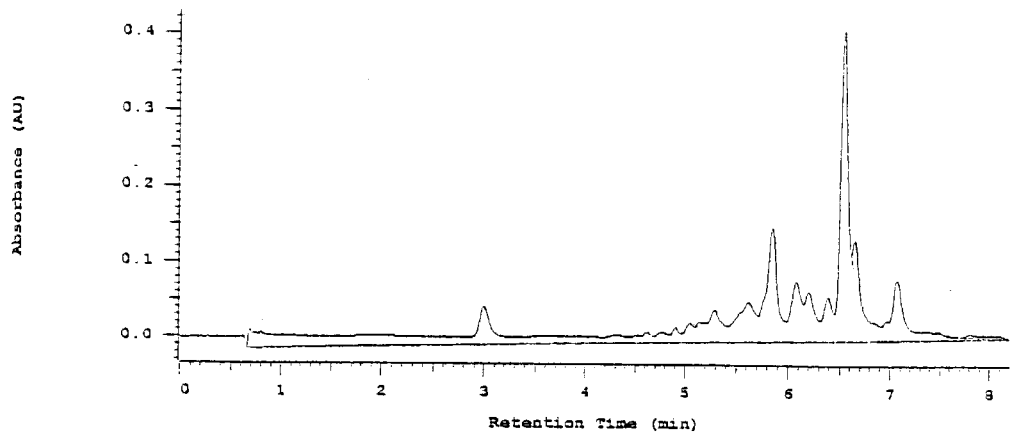
FIGS. 5a–5b show reverse-phase HPLC chromatograms of 5' H$_2$N-(PEO)$_2$-AAA ATC AAG AAC TAC AAG ACC GCC C 3' (SEQ ID. NO. 6) cleaved and deprotected with concentrated NH4OH only (FIG. 5a) and with 1% diethylmalonate (DEM) in 15% ethanol:NH$_4$OH (FIG. 5b).
Figure 5B:
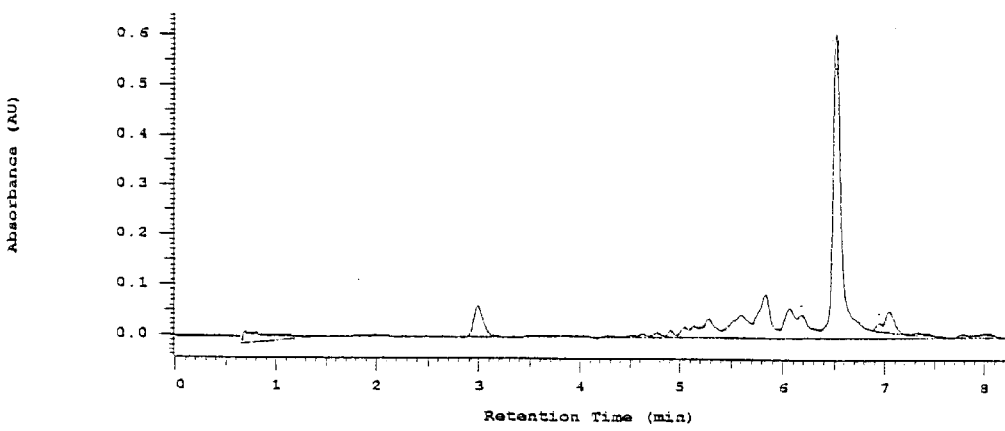

Following the Procedures of Example 3, the 25 nt Oligonucleotide:

5' H$_2$N-(PEO)$_2$-AAA ATC AAG AAC TAC AAG ACC GCC C 3' (SEQ ID. NO. 6)

was synthesized on C polystyrene support. After the final A phosphoramidite was coupled, two PEO (pentaethyleneoxy; —(CH$_2$CH$_2$O)$_5$—) linkers were coupled as PEO phosphoramidite, followed by Aminolink TFA (Applied Biosystems, Foster City, Calif.) phosphoramidite to give the 5' amino with 2 PEO linkages (Vinayak, WO 00/50432; Andrus, WO 98/39353). The support was divided into two portions. One portion was cleaved and deprotected with NH$_4$OH only. The other portion was cleaved an deprotected with 1% DEM in 15% ethanol:NH$_4$OH. An aliquot from each portion was analyzed by reverse phase HPLC. The portion cleaved and deprotected with NH4OH only shows a complex product mixture containing only 25.8% of the desired product eluting at 6.5 minutes (FIG. 5a). The product mixture is contaminated with significant later eluting impurities. The portion cleaved and deprotected with 1% DEM shows improved purity, 48.9% of the desired product eluting at 6.5 minutes and diminished levels of earlier and later eluting impurities (FIG. 5b).

All publications, patents, and patent applications referred to herein are hereby incorporated by reference, and to the same extent as if each individual publication, patent or patent application was specifically and individually indicated to be incorporated by reference.

Although only a few embodiments have been described in detail above, those having ordinary skill in the chemical arts will clearly understand that many modifications are possible in these embodiments without departing from the teachings thereof. All such modifications are intended to be encompassed within the scope of the following claims.

I claim:

1. A method for deprotection of an oligonucleotide containing at least one 2-cyanoethyl phosphate internucleotide linkage, the method comprising the step of
reacting the protected oligonucleotide with a deprotection reagent comprising an active methylene compound and an amine reagent,
wherein the active methylene compound comprises at least one of a 1,3 keto-ester, a 1,3 diketone, malononitrile, malonic acid, malonamide, or a dialkylmalonate diester wherein the alkyl groups are $C_1$–$C_6$ alkyl,

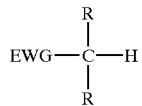

whereby protecting groups are removed from the oligonucleotide.

2. The method of claim 1 wherein the protected oligonucleotide is covalently attached to a solid support through a linkage.

3. The method of claim 2 further comprising the step of cleaving the oligonucleotide from the solid support.

4. The method of claim 2 wherein the oligonucleotide remains covalently attached to the solid support after reacting with the deprotection reagent.

5. The method of claim 2 wherein the solid support comprises highly cross-linked polystyrene.

6. The method of claim 2 wherein the solid support comprises controlled-pore-glass.

7. The method of claim 2 wherein the solid support is a membrane which allows the deprotection reagent to pass through.

8. The method of claim 2 wherein the solid support is a frit which allows the deprotection reagent to pass through.

9. The method of claim 2 wherein the solid support is a planar, non-porous material.

10. The method of claim 9 wherein the material is glass, quartz, or diamond.

11. The method of claim 9 wherein the material is polystyrene, polyethylene, polypropylene, nylon, graft of polystyrene and polyethylene glycol, copolymer of ethylene and acrylate, or copolymer of ethylene and methacrylate.

12. The method of claim 2 wherein the solid support is positioned in a column having inlet and outlet openings whereby reagents may flow through the column.

13. The method of claim 12 further comprising placing a plurality of such columns in a holder and concurrently deprotecting a plurality of oligonucleotides.

14. The method of claim 13 wherein the holder is a microtiter plate having an array of such columns.

15. The method of claim 1 wherein the protected oligonucleotide comprises a nucleic acid analog.

16. The method of claim 15 wherein the nucleic acid analog is LNA.

17. The method of claim 15 wherein the nucleic acid analog is PNA.

18. The method of claim 15 wherein the nucleic acid analog is 2'-O-methyl RNA.

19. The method of claim 1 wherein the protected oligonucleotide is covalently attached to a label.

20. The method of claim 19 wherein the label is selected from the group consisting of a fluorescent dye, a quencher, biotin, a mobility-modifier, a minor groove binder, and a linker selected from $C_1$–$C_6$ alkylamine and $C_1$–$C_6$ alkylthiol.

21. The method of claim 20 wherein the protected oligonucleotide comprises a minor groove binder that is CDPI-3.

22. The method of claim 20 wherein the fluorescent dye is a fluorescein, a rhodamine, or a cyanine dye.

23. The method of claim 19 wherein the label is attached to the 5'-terminus of the polynucleotide.

24. The method of claim 19 wherein the label is attached to the 3'-terminus of the polynucleotide.

25. The method of claim 1 wherein the deprotection reagent further comprises water.

26. The method of claim 1 wherein the deprotection reagent further comprises an alcohol solvent.

27. The method of claim 26 wherein the alcohol solvent is methanol.

28. The method of claim 26 wherein the alcohol solvent is ethanol.

29. The method of claim 26 wherein the alcohol solvent is ethylene glycol.

30. The method of claim 1 wherein the active methylene compound is 2,4-pentanedione.

31. The method of claim 1 wherein the active methylene compound is 1,3-cyclohexanedione.

32. The method of claim 1 wherein the active methylene compound is ethyl acetoacetate.

33. The method of claim 1 wherein the active methylene compound is malononitrile.

34. The method of claim 1 wherein the active methylene compound is malonic acid.

35. The method of claim 1 wherein the active methylene compound is malonamide.

36. The method of claim 1 wherein the active methylene compound is a dialkylmalonate diester wherein the alkyl groups are $C_1$–$C_6$ alkyl.

37. The method of claim 36 wherein the deprotection reagent comprises aqueous ammonium hydroxide, and an alcohol solvent.

38. The method of claim 37 wherein the dialkylmalonate diester is dimethylmalonate.

39. The method of claim 37 wherein the dialkylmalonate diester is diethylmalonate.

40. The method of claim 37 wherein the dialkylmalonate diester is di-n-propylmalonate.

41. The method of claim 37 wherein the dialkylmalonate diester is diisopropylmalonate.

42. The method of claim 1 wherein the amine reagent is aqueous ammonium hydroxide.

43. The method of claim 1 wherein the amine reagent is aqueous methylamine.

44. The method of claim 1 wherein the amine reagent is ethylamine.

45. The method of claim 1 wherein the amine reagent is isopropylamine.

46. The method of claim 1 wherein the amine reagent is n-propylamine.

47. The method of claim 1 wherein the amine reagent is n-butylamine.

48. The method of claim 1 wherein the amine reagent is 1,2-ethylenediamine.

49. The method of claim 1 wherein the amine reagent is 1,8-diazabi-cyclo[5.4.0]undec-7-ene (DBU) or 1,5-diazabicyclo[4.3.0]non-5-ene (DBN).

50. The method of claim 2 wherein said reacting step is effected by: wetting the protected oligonucleotide covalently attached to the solid support with an active methylene compound and a solvent, and then treating the protected oligonucleotide with an amine reagent.

51. The method of claim 50 wherein the solid support is confined in a column having inlet and outlet openings whereby reagents may flow through the column.

52. The method of claim 51 wherein a plurality of columns are configured in a holder whereby a plurality of oligonucleotides are deprotected concurrently.

53. The method of claim 52 wherein the holder is in a microtiter well configuration of equally spaced columns.

54. The method of claim 50 further comprising the step wherein the protected oligonucleotide and the amine reagent are, placed in a sealable vessel whereby the oligonucleotide is deprotected.

55. The method of claim 50 wherein the amine reagent is aqueous ammonium hydroxide.

56. The method of claim 50 wherein the amine reagent is ammonia gas.

57. The method of claim 50 wherein the amine reagent is a $C_1$–$C_6$ alkylamine.

58. The method of claim 50 wherein the solvent is an alcohol, an ether, an amide, acetonitrile, dichloromethane, or dimethylsulfoxide.

59. The method of claim 58 wherein the alcohol is methanol, ethanol, n-propanol, isopropanol, or 1,2-ethylene glycol.

60. The method of claim 58 wherein the ether is diethyl ether, tetrahydrofuran, 1,4-dioxane, or 1,2-dimethoxyethane.

61. The method of claim 58 wherein the amide is acetamide, formamide, benzamide, or dimethylformamide.

* * * * *

UNITED STATES PATENT AND TRADEMARK OFFICE
CERTIFICATE OF CORRECTION

PATENT NO. : 6,664,388 B2
DATED : December 16, 2003
INVENTOR(S) : Jeffrey S. Nelson It is certified that error appears in the above-identified patent and that said Letters Patent is hereby corrected as shown below:

Column 25,
Lines 33-37, please delete the chemical structure below:

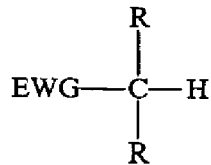

Signed and Sealed this

Eighth Day of February, 2005

JON W. DUDAS
*Director of the United States Patent and Trademark Office*